US012121463B1

(12) United States Patent
Solotoff

(10) Patent No.: US 12,121,463 B1
(45) Date of Patent: Oct. 22, 2024

(54) KNEE/ELBOW BRACE

(71) Applicant: Preferred Prescription, Inc., Hollywood, FL (US)

(72) Inventor: Brandon Solotoff, Boca Raton, FL (US)

(73) Assignee: Preferred Prescription, Inc., Hollywood, FL (US)

( * ) Notice: Subject to any disclaimer, the term of this patent is extended or adjusted under 35 U.S.C. 154(b) by 866 days.

(21) Appl. No.: 17/166,161

(22) Filed: Feb. 3, 2021

Related U.S. Application Data

(60) Provisional application No. 62/975,925, filed on Feb. 13, 2020.

(51) Int. Cl.
*A61F 5/01* (2006.01)
(52) U.S. Cl.
CPC .......... *A61F 5/0109* (2013.01); *A61F 5/0125* (2013.01)
(58) Field of Classification Search
CPC ........ A61F 5/0106; A61F 5/0109; A61F 5/01; A61F 5/0102; A61F 5/0104; A61F 5/0123; A61F 5/0125
See application file for complete search history.

(56) References Cited

U.S. PATENT DOCUMENTS

| 58,403 | A | 10/1866 | Goodwin |
|---|---|---|---|
| 1,257,297 | A | 2/1918 | Brown |
| 1,510,408 | A | 9/1924 | Lychou |
| 1,622,211 | A | 3/1927 | Sheehan |
| 2,144,641 | A | 1/1939 | Snyder |
| 2,195,024 | A | 3/1940 | Bullock |
| 2,270,685 | A | 1/1942 | Miller |

(Continued)

FOREIGN PATENT DOCUMENTS

| CN | 203915158 U | 11/2014 |
|---|---|---|
| CN | 105443565 B | 3/2016 |

(Continued)

OTHER PUBLICATIONS

Bracelayer Knee Stabilizing Compression Pants, "How to Stop Your Knee Brace from Slipping Down," Oct. 4, 2018; available at: https://USA.bracelayer.com/blogs/knee-news/how-to-stop-your-knee-brace-from-slipping-down.

(Continued)

*Primary Examiner* — Keri J Nelson
(74) *Attorney, Agent, or Firm* — Thomas A. O'Rourke; James Bongiorno; O'Rourke IP Law, PLLC

(57) ABSTRACT

A knee brace includes an elastic material having: a first portion with first and second ends fixedly secured together forming a sleeve to encircle a leg below the knee, applying compression thereto, and second portion with first and second ends spaced apart forming first and second flaps that wrap around the wearer's leg above the knee, with the first flap overlapping onto and releasably securing to the second flap using hook and loop materials, to apply compression thereto. A secondary flap is fixedly secured to the upper portion, with its free end releasably secured to the second flap using hook or loop materials, to apply compression thereto. The first flap is angled upwardly and the secondary flap is angled downwardly for respective securement to the second flap. These redundant securements at the divergent angles better maintains the brace at the proper positioning on the wearer's leg.

6 Claims, 24 Drawing Sheets

(56) References Cited

U.S. PATENT DOCUMENTS

| | | |
|---|---|---|
| 2,308,776 A | 1/1943 | Peckham |
| 2,467,907 A | 4/1949 | Peckham |
| 2,587,166 A | 2/1952 | Jovick |
| 2,959,168 A | 11/1960 | Shook |
| 3,046,981 A | 7/1962 | Biggs |
| 3,194,233 A | 7/1965 | Peckham |
| 3,350,719 A | 11/1967 | McClure |
| 3,528,412 A | 9/1970 | McDavid |
| 3,575,166 A | 4/1971 | Rosman |
| 3,581,741 A | 6/1971 | Rosman |
| 3,587,572 A | 6/1971 | Evans |
| 3,662,435 A | 5/1972 | Allsop |
| 3,698,389 A | 10/1972 | Guedel |
| 3,749,366 A | 7/1973 | Brucker |
| 3,785,371 A | 1/1974 | Lewis |
| 3,799,158 A | 3/1974 | Gardner |
| 3,817,244 A | 6/1974 | Taylor |
| 3,826,251 A | 7/1974 | Ross |
| 3,970,081 A | 7/1976 | Applegate |
| 4,088,130 A | 5/1978 | Applegate |
| 4,090,508 A | 5/1978 | Gaylord |
| 4,116,236 A | 9/1978 | Albert |
| 4,176,665 A | 12/1979 | Terpening |
| 4,185,360 A | 1/1980 | Prete |
| 4,201,203 A | 5/1980 | Applegate |
| 4,215,687 A | 8/1980 | Shaw |
| 4,219,892 A | 9/1980 | Rigdon |
| 4,240,414 A | 12/1980 | Theisler |
| 4,256,097 A | 3/1981 | Willis |
| 4,271,831 A | 6/1981 | Deibert |
| 4,275,716 A | 6/1981 | Scott |
| 4,287,885 A | 9/1981 | Applegate |
| 4,353,362 A | 10/1982 | DeMarco |
| 4,366,813 A | 1/1983 | Nelson |
| 4,370,977 A | 2/1983 | Mauldin |
| 4,370,978 A | 2/1983 | Palumbo |
| 4,372,298 A | 2/1983 | Lerman |
| 4,381,768 A | 5/1983 | Erichsen |
| D269,379 S | 6/1983 | Bledsoe |
| 4,387,709 A | 6/1983 | Shen |
| 4,428,369 A | 1/1984 | Peckham |
| 4,433,679 A | 2/1984 | Mauldin |
| 4,445,505 A | 5/1984 | Labour |
| 4,487,200 A | 12/1984 | Feanny |
| 4,493,316 A | 1/1985 | Reed |
| 4,506,661 A | 3/1985 | Foster |
| 4,520,804 A | 6/1985 | DiGeorge |
| 4,523,585 A | 6/1985 | Lamb |
| 4,524,764 A | 6/1985 | Miller |
| 4,554,913 A | 11/1985 | Womack |
| 4,556,053 A | 12/1985 | Irons |
| 4,572,170 A | 2/1986 | Cronk |
| 4,576,151 A | 3/1986 | Carmichael |
| 4,604,770 A | 8/1986 | Lang |
| 4,607,628 A | 8/1986 | Dashefsky |
| 4,624,247 A | 11/1986 | Ford |
| 4,628,916 A | 12/1986 | Lerman |
| 4,632,096 A | 12/1986 | Harris |
| 4,632,098 A | 12/1986 | Grundei |
| 4,633,867 A | 1/1987 | Kausek |
| 4,686,969 A | 8/1987 | Scott |
| 4,726,362 A | 2/1988 | Nelson |
| 4,732,143 A | 3/1988 | Kausek |
| 4,738,252 A | 4/1988 | Friddle |
| 4,751,920 A | 6/1988 | Mauldin |
| 4,768,500 A | 9/1988 | Mason |
| 4,791,916 A | 12/1988 | Paez |
| 4,796,610 A | 1/1989 | Cromartie |
| 4,803,975 A | 2/1989 | Meyers |
| 4,805,606 A | 2/1989 | McDavid |
| 4,817,588 A | 4/1989 | Bledsoe |
| 4,822,371 A | 4/1989 | Jolly |
| 4,838,251 A | 6/1989 | Chignor |
| 4,846,842 A | 7/1989 | Connolly |
| 4,854,308 A | 8/1989 | Drillio |
| 4,856,501 A | 8/1989 | Castillo |
| 4,870,956 A | 10/1989 | Fatool |
| 4,872,448 A | 10/1989 | Johnson |
| 4,928,670 A | 5/1990 | DeLorenzo |
| 4,928,676 A | 5/1990 | Pansiera |
| 4,938,207 A | 7/1990 | Vargo |
| 4,940,044 A | 7/1990 | Castillo |
| 4,955,369 A | 9/1990 | Bledsoe |
| 4,961,416 A | 10/1990 | Moore |
| 4,966,133 A | 10/1990 | Kausek |
| 4,982,732 A | 1/1991 | Morris |
| 4,986,264 A | 1/1991 | Miller |
| 5,000,169 A | 3/1991 | Swicegood |
| 5,009,223 A | 4/1991 | DeFonce |
| 5,016,621 A | 5/1991 | Bender |
| 5,018,514 A | 5/1991 | Grood |
| 5,022,391 A | 6/1991 | Weidenburner |
| 5,025,782 A | 6/1991 | Salerno |
| 5,038,763 A | 8/1991 | Wiggins |
| 5,039,247 A | 8/1991 | Young |
| 5,042,464 A | 8/1991 | Skwor |
| 5,060,640 A | 10/1991 | Rasmusson |
| 5,062,858 A | 11/1991 | Broeck |
| 5,063,913 A | 11/1991 | Nyi |
| 5,063,916 A | 11/1991 | France |
| 5,078,127 A | 1/1992 | Daneman |
| 5,086,760 A | 2/1992 | Neumann |
| 5,092,320 A | 3/1992 | Maurer |
| 5,107,824 A | 4/1992 | Rogers |
| 5,135,469 A | 8/1992 | Castillo |
| 5,168,865 A | 12/1992 | Radcliffe |
| 5,188,584 A | 2/1993 | Petrofsky |
| 5,230,696 A | 7/1993 | Silver |
| 5,267,946 A | 12/1993 | Singer |
| 5,277,697 A | 1/1994 | France |
| 5,277,698 A | 1/1994 | Taylor |
| 5,288,287 A | 2/1994 | Castillo |
| 5,302,169 A | 4/1994 | Taylor |
| 5,330,418 A | 7/1994 | Townsend |
| 5,352,190 A | 10/1994 | Fischer |
| 5,356,370 A | 10/1994 | Fleming |
| 5,358,469 A | 10/1994 | Patchel |
| 5,383,843 A | 1/1995 | Watson |
| 5,403,002 A | 4/1995 | Brunty |
| 5,407,420 A | 4/1995 | Bastyr |
| 5,409,449 A | 4/1995 | Nebolon |
| 5,419,754 A | 5/1995 | Hutchins |
| 5,421,810 A | 6/1995 | Davis |
| 5,443,444 A | 8/1995 | Pruyssers |
| 5,458,565 A | 10/1995 | Tillinghast |
| 5,460,599 A | 10/1995 | Davis |
| 5,472,410 A | 12/1995 | Hamersly |
| 5,490,831 A | 2/1996 | Myers |
| 5,527,268 A | 6/1996 | Gildersleeve |
| 5,554,104 A | 9/1996 | Grim |
| 5,558,627 A | 9/1996 | Singer |
| 5,586,970 A | 12/1996 | Morris |
| 5,641,322 A | 6/1997 | Silver |
| 5,658,243 A | 8/1997 | Miller |
| 5,672,152 A | 9/1997 | Mason |
| 5,743,865 A | 4/1998 | Townsend |
| 5,782,785 A | 7/1998 | Herzberg |
| 5,792,084 A | 8/1998 | Wilson |
| 5,797,864 A | 8/1998 | Taylor |
| 5,800,371 A | 9/1998 | Winn |
| 5,807,294 A | 9/1998 | Cawley |
| 5,814,000 A | 9/1998 | Kilby |
| 5,817,040 A | 10/1998 | Hess |
| 5,823,931 A | 10/1998 | Gilmour |
| 5,857,989 A | 1/1999 | Smith |
| 5,865,776 A | 2/1999 | Springs |
| 5,865,777 A | 2/1999 | Detty |
| 5,873,847 A | 2/1999 | Bennett |
| 5,873,848 A | 2/1999 | Fulkerson |
| 5,938,629 A | 8/1999 | Bloedau |
| 5,997,493 A | 12/1999 | Young |
| 6,074,355 A | 6/2000 | Bartlett |
| 6,110,138 A | 8/2000 | Shirley |
| 6,203,511 B1 | 3/2001 | Johnson |

(56) References Cited

U.S. PATENT DOCUMENTS

| | | |
|---|---|---|
| 6,290,664 B1 | 9/2001 | Nauert |
| 6,402,711 B1 | 6/2002 | Nauert |
| 6,402,713 B1 | 6/2002 | Doyle |
| 6,413,232 B1 | 7/2002 | Townsend |
| 6,527,733 B1 | 3/2003 | Ceriani |
| 6,540,709 B1 | 4/2003 | Smits |
| 6,547,218 B2 | 4/2003 | Landy |
| 6,610,023 B1 | 8/2003 | Steponovich |
| 6,689,080 B2 | 2/2004 | Castillo |
| 6,773,411 B1 | 8/2004 | Alvarez |
| 6,878,126 B2 | 4/2005 | Nelson |
| 6,993,808 B1 | 2/2006 | Bennett |
| 6,994,682 B2 | 2/2006 | Bauerfeind |
| 7,004,919 B2 | 2/2006 | Gaylord |
| 7,037,287 B2 | 5/2006 | Cormier |
| 7,059,329 B2 | 6/2006 | Mason |
| 7,122,016 B1 | 10/2006 | DeToro |
| 7,150,721 B2 | 12/2006 | Houser |
| 7,189,212 B2 | 3/2007 | Popp |
| 7,198,610 B2 | 4/2007 | Infimundarson |
| 7,201,728 B2 | 4/2007 | Sterling |
| 7,217,249 B2 | 5/2007 | Scott |
| 7,235,059 B2 | 6/2007 | Mason |
| 7,285,103 B2 | 10/2007 | Nathanson |
| 7,306,572 B2 | 12/2007 | Ceriani |
| D573,713 S | 7/2008 | Mueller |
| 7,431,708 B2 | 10/2008 | Sreeramagiri |
| 7,473,234 B1 | 1/2009 | Weltner |
| 7,597,675 B2 | 10/2009 | Ingimundarson |
| 7,615,021 B2 | 11/2009 | Nordt |
| 7,691,074 B2 | 4/2010 | Nordt |
| 7,704,218 B2 | 4/2010 | Einarsson |
| 7,713,225 B2 | 5/2010 | Ingimundarson |
| 7,794,418 B2 | 9/2010 | Ingimundarson |
| 7,819,830 B2 | 10/2010 | Sindel |
| 7,867,183 B2 | 1/2011 | Kazmierczak |
| 7,892,195 B2 | 2/2011 | Grim |
| D634,437 S | 3/2011 | Gramza |
| 7,896,827 B2 | 3/2011 | Ingimundarson |
| 7,984,531 B2 | 7/2011 | Moore |
| 7,988,653 B2 | 8/2011 | Fout |
| 8,016,781 B2 | 9/2011 | Ingimundarson |
| D646,790 S | 10/2011 | Castillo |
| 8,062,242 B2 | 11/2011 | Ceriani |
| 8,104,141 B2 | 1/2012 | Yamashita |
| 8,172,781 B2 | 5/2012 | Oddou |
| 8,231,560 B2 | 7/2012 | Ingimundarson |
| 8,241,234 B2 | 8/2012 | Ingimundarson |
| 8,257,293 B2 | 9/2012 | Ingimundarson |
| 8,277,401 B2 | 10/2012 | Hammerslag |
| 8,591,444 B2 | 11/2013 | Bejarano |
| 8,728,018 B2 | 5/2014 | McCune |
| 8,808,211 B2 | 8/2014 | Paulos |
| 8,858,482 B2 | 10/2014 | Ingimundarson |
| 8,864,692 B2 | 10/2014 | Ingimundarson |
| 8,882,689 B2 | 11/2014 | Castillo |
| 8,926,539 B2 | 1/2015 | Cropper |
| 9,125,730 B2 | 9/2015 | Ingimundarson |
| 9,265,645 B2 | 2/2016 | Ingimundarson |
| 9,351,864 B2 | 5/2016 | Romo |
| 9,458,878 B2 | 10/2016 | Scatassa |
| 10,052,221 B2 * | 8/2018 | Albertsson ............ A61F 5/0109 |
| 10,143,581 B2 | 12/2018 | Chetlapalli |
| 10,206,804 B1 * | 2/2019 | Pahls ................... A61F 5/0123 |
| 2003/0149386 A1 | 8/2003 | Ceriani |
| 2004/0225245 A1 | 11/2004 | Nelson |
| 2004/0267179 A1 | 12/2004 | Lerman |
| 2005/0192523 A1 | 9/2005 | Knecht |
| 2006/0100561 A1 | 5/2006 | Gilmour |
| 2006/0206045 A1 | 9/2006 | Townsend |
| 2007/0010772 A1 | 1/2007 | Ryan |
| 2007/0213648 A1 | 9/2007 | Ferrigolo |
| 2009/0131844 A1 | 5/2009 | Dean |
| 2009/0259154 A1 | 10/2009 | Nace |
| 2009/0287125 A1 | 11/2009 | Ingimundarson |
| 2009/0299244 A1 | 12/2009 | Chiang |
| 2011/0000097 A1 | 1/2011 | Chan |
| 2013/0190669 A1 | 7/2013 | Rokosz |
| 2014/0124557 A1 | 5/2014 | Velare |
| 2014/0148747 A1 | 5/2014 | Fleming |
| 2016/0040464 A1 | 2/2016 | Lu |

FOREIGN PATENT DOCUMENTS

| | | |
|---|---|---|
| DE | 19904554 B4 | 8/2000 |
| DE | 60035431 T2 | 3/2008 |
| DE | 102012002554 A1 | 8/2013 |
| EP | 2260799 A1 | 12/2010 |
| EP | 3378448 A2 | 9/2018 |
| GB | 2136294 A | 9/1984 |
| GB | 2163352 A | 2/1986 |
| KR | 20180082516 A | 7/2018 |

OTHER PUBLICATIONS

Shalmali Pal, Lower Extremity Review Magazine, "Minimizing the Effects of Knee Brace Migration," Jun. 2012, available at: https://lermagazine.com/article/minimizing-the-effects-of-knee-brace-migration.

Press Fit Forces Stress Design Calculator, Jun. 18, 2018, available at: www.engineersedge.com/calculators/machine-design/press-fit/press-fit.htm.

"Three General Types of Fit," available at www.mmto.org/dclark/Reports/Encoder %20Upgrade/fittolerences%20%5BRead-Only%5D.pdf., Jul. 8, 2019.

"Engineering Fit," available at: https://en.wikipedia.org/wiki/Engineering_fit, Jul. 8, 2019.

* cited by examiner

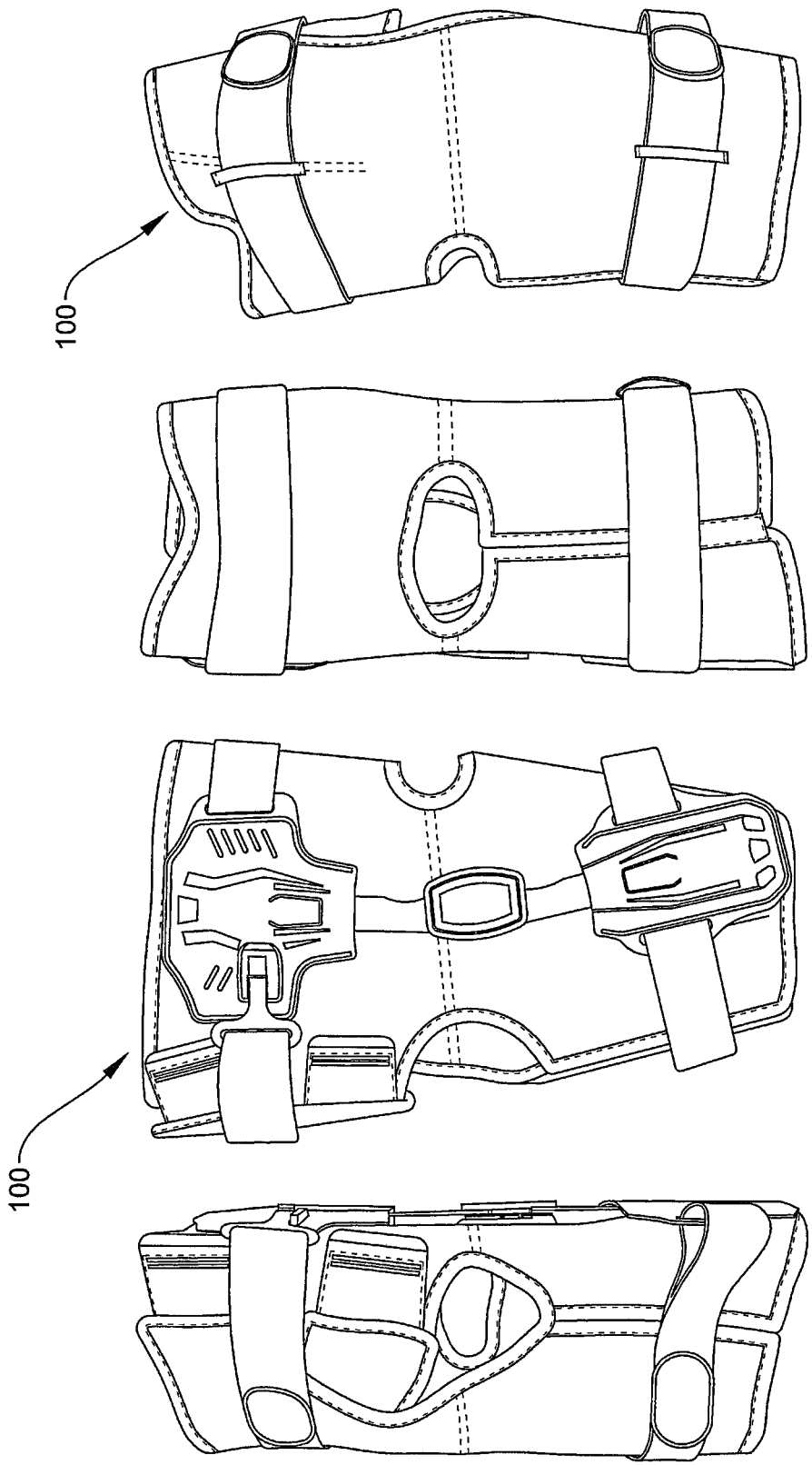

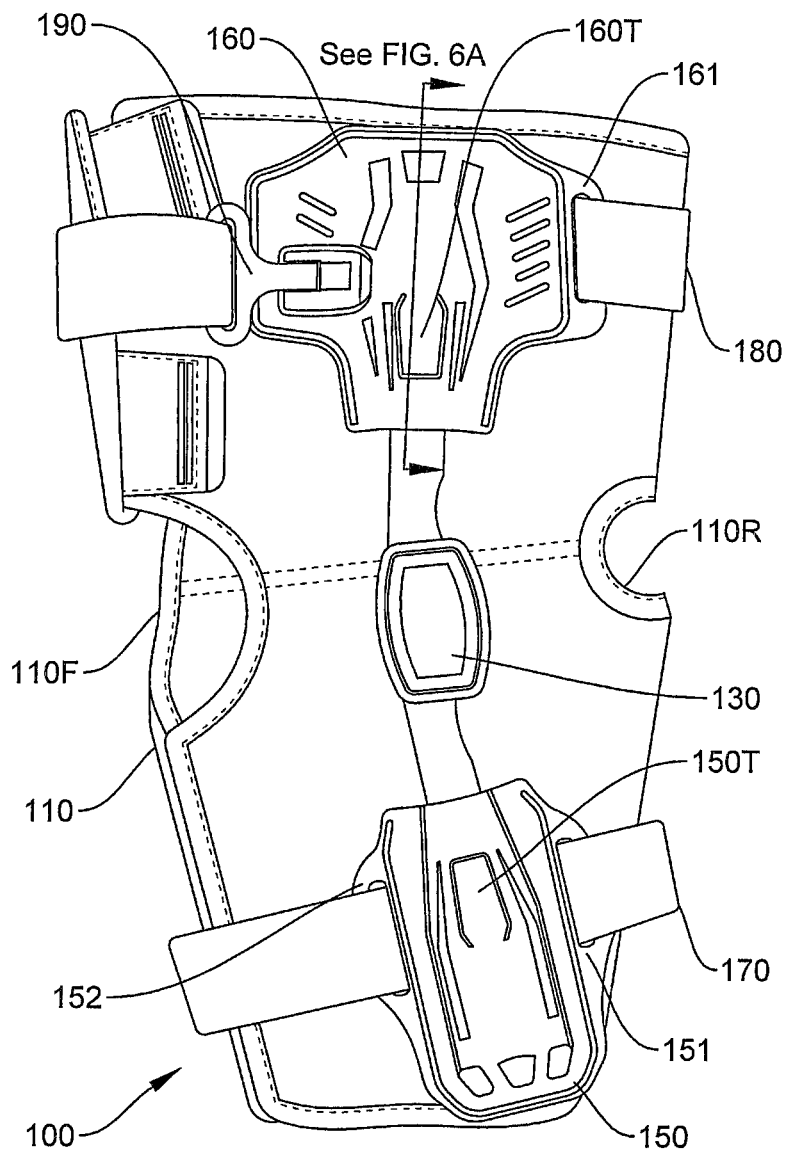
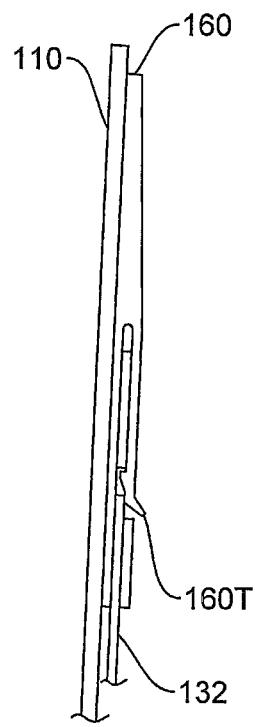
FIG. 6
FIG. 6A

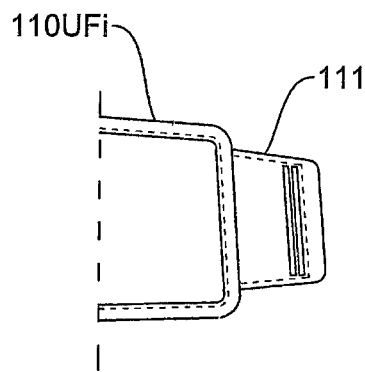
FIG. 12A
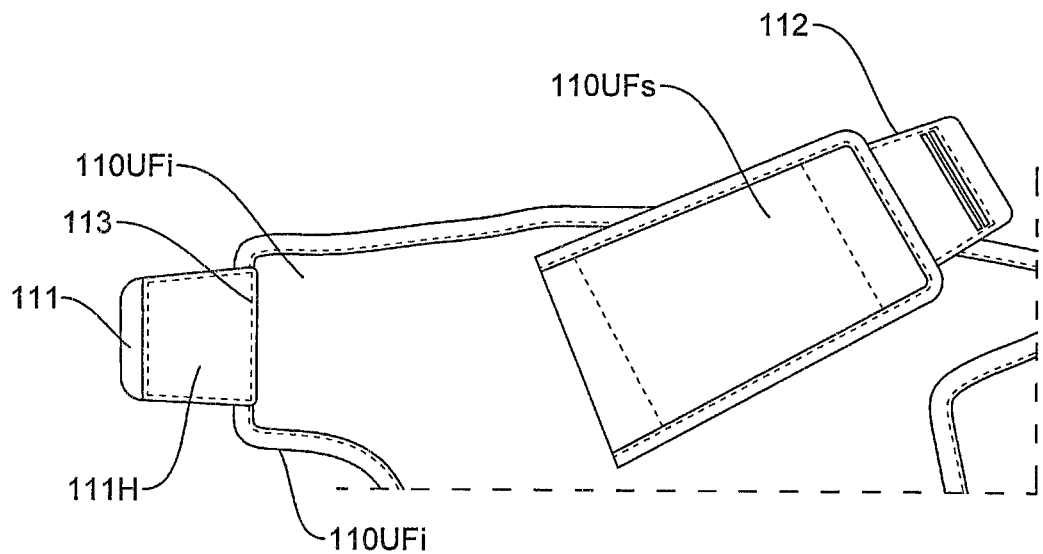
FIG. 12B
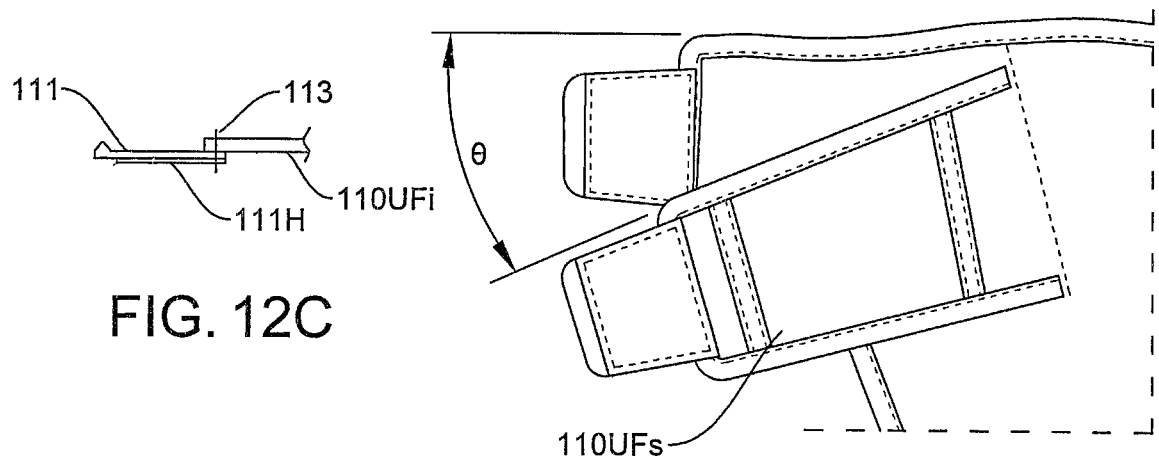
FIG. 12C
FIG. 12D

KNEE/ELBOW BRACE

CROSS REFERENCES TO RELATED APPLICATIONS

This application claims priority on U.S. Provisional Application Ser. No. 62/975,925, filed on Feb. 13, 2020, the disclosures of which are incorporated herein by reference.

FIELD OF THE INVENTION

This disclosure relates generally to orthotic devices, and more particularly to a knee or elbow orthosis that may use a polycentric hinge that is replaceable, and may have a double securement arrangement for securing the upper portion of the brace to the limb of the wearer above the joint to prevent downward migration.

BACKGROUND OF THE INVENTION

Although there are many reasons for a person to wear a knee brace, the most common reason does not relate to an existing leg injury; conversely a knee brace is most commonly worn/utilized to protect the wearer's otherwise healthy knee from becoming injured. Many athletes and other people that may be at risk of a knee injury tend to wear a brace as a preventative measure—the knee brace helps prevent the wearer's knee joint from being forced into a position that would tend to cause an injury, including, but not limited to, twisting or overextending of the knee. In these cases, the brace is referred to as a functional brace, as it is utilized while the athlete's knee is still fully functional.

A knee brace that is not utilized as a preventative measure, is instead worn to address one or more issues relating to an injury. For example, a knee brace may be worn while recovering from an injury to help ensure complete healing and strengthening of the knee joint when it has not yet returned to its pre-injury condition. Such a brace is referred to as a rehabilitative brace, and may serve to provide stability, support, and protection for the knee against an aggravating event that could result in greater injury to the knee than was initially suffered. The rehabilitative knee brace may also be worn to prevent or limit swelling that typically occurs with a knee injury. The standard "RICE" method for treating an injury calls for rest, ice, compression, and elevation. While the need for rest (i.e., putting little or no weight on the injured region) enables healing and prevents further injury, the steps of applying ice and compression to the injury and of elevating the injured limb are each directed to multiple aspects of the recovery that includes reducing and/or preventing further swelling of that region. Therefore, in compliance with the RICE method, a brace is therefore also worn to address the need for compression to reduce swelling of and around the injured knee joint.

Additionally, a knee brace is often worn to provide support/stability, to decrease pain, and enable greater functioning of a wearer's knee that may be afflicted from arthritis, whether osteoarthritis or inflammatory arthritis. Such knee brace wearers may find that any one of the different types of braces provide relief. For example, some patients with knee arthritis find benefits/relief from wearing a simple compressive wrap (i.e., a knee sleeve with an opening for the patella but without any hinge-see e.g., U.S. Pat. No.: 4,084,584 to Detty; and U.S. Pat. No. 5,139,477 to Peters). Some patients with knee arthritis find benefits/relief from wearing a patellofemoral brace that has pads or particular support surrounding the knee joint, which may prevent lateral subluxation (see e.g., U.S. Pat. No.: 4,607,628 to Dashefsky; U.S. Pat. No. 6,551,264 to Cawley; U.S. Pat. No. 7,083,586 to Simmons; and U.S. Pat. No. 9,113,998 to Romo). Other patients with knee arthritis find benefits/relief from wearing an unloader brace that is custom designed for the wearer and serves to shift stress away from the part of the knee with arthritis (i.e., shifting stress from the arthritic side to the other healthier side of the leg-see e.g., U.S. Pat. No. 9,610,188 to Walsh for a "VRB Cantilever-Based Unloader Brace Assembly"; and U.S. Patent Application Pub. No. 2018/0140505 (Barati) for "Vibratory Unloading Knee Brace for Knee Osteoarthritis"). Yet other patients with knee arthritis find benefits/relief from wearing a functional brace that has hinges (see e.g., U.S. Pat. No.: 4,372,298 to Lerman; U.S. Pat. No. 4,493,316 to Reed; U.S. Pat. No. 4,732,143 to Kausek; U.S. Pat. No. 4,986,264 to Miller; U.S. Pat. No. 5,358,469 to Patchel; U.S. Pat. No. 5,419,754 to Hutchins; U.S. Pat. No. 6,402,713 to Doyle; and U.S. Pat. No. 6,527,733 to Ceriani). It is noted that citing within this disclosure of any patents, published patent applications, and non-patent literature is not an admission as to any of those references constituting prior art with respect to the herein disclosed and claimed apparatus.

The wearer of a particular knee brace may experience several different problems, even where the brace is properly sized and suited for the person. One problem that persists is how to secure the brace to the leg, so that it does not tend to slide down. Most knee braces do not stay at the desired/optimal position at which they are initially secured, and distal knee brace migration can have a detrimental effect upon the efficacy of the support and stability that the brace is designed to provide. See e.g., Bracelayer Knee Stabilizing Compression Pants, "How to Stop Your Knee Brace from Slipping Down," Oct. 4, 2018; and Lower Extremity Review Magazine, "Minimizing the Effects of Knee Brace Migration," Shalmali Pal, June 2012.

The herein disclosed apparatus provides improvements upon certain prior art knee braces, including, but not limited to, an improved upper strap securement arrangement that better prevents sliding down of the brace while being worn by the wearer.

OBJECTS OF THE INVENTION

It is an object of the invention to provide an improved knee orthosis.

It is another object of the invention to provide a knee brace that provides improved support for the knee joint and greater stability for the leg of the wearer.

It is a further object of the invention to provide a knee brace that prevents slipping of the brace downward while being worn by the wearer.

It is another object of the invention to provide a knee brace with an improved attachment arrangement for releasably securing the upper portion of the brace above the wearer's knee to the thigh region.

It is also an object of the invention to provide a knee brace with an upper attachment strap that may traverse around an upper loop to secure to itself using hook and loop materials, and which loop may also be releasably attached to the brace using a quick release coupling.

Further objects and advantages of the invention will become apparent from the following description and claims, and from the accompanying drawings.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

A first knee brace embodiment as disclosed herein may broadly include an elastic material. A first portion of the elastic material is formed to have first and second ends spaced apart a first distance, which ends are fixedly secured together to form a sleeve configured to encircle a leg of the wearer below the knee, to apply a first level of compression thereto. A second portion of the elastic material is formed to have first and second ends spaced apart a second distance and are configured to form a first flap and a second flap, such that the second portion of the elastic material may be circumferentially wrapped around the leg of the wearer above the knee, with the second distance being sufficient for the first flap to thereat overlap onto the second flap. Hook and loop materials on the first and second flaps are used to releasably secure the first flap to the second flap, to apply a second level of compression thereto. A secondary flap may have a first end fixedly secured to the upper portion of the elastic material, with the secondary flap having a length sufficient so that a second thereof may be releasably secured to the second flap using hook or loop materials, to apply a third level of compression thereto.

The first flap may be formed to be angled upwardly for the securement to the second flap, and the secondary flap is attached and shaped to be angled downwardly for its securement to the second flap. These redundant securements at the divergent angles better helps to maintain the brace at the proper (initial) positioning on the wearer's leg.

In one embodiment, the first flap may be angled upwardly with respect to a traverse plane (i.e., a plane that cuts the body into top and bottom portions) in the range of five degrees to eight degrees; and the secondary flap may be angled downwardly with respect to a traverse plane in the range of five degrees to eight degrees. In another embodiment, the first flap may be angled upwardly with respect to a traverse plane in the range of eight degrees to twelve degrees; and the secondary flap may be angled downwardly with respect to a traverse plane in the range of eight degrees to twelve degrees. In yet another embodiment, the first flap may be angled upwardly with respect to a traverse plane in the range of twelve degrees to fifteen degrees; and the secondary flap may be angled downwardly with respect to a traverse plane in the range of twelve degrees to fifteen degrees. In other embodiments, a combination of those ranges, or other ranges for the angles may alternatively be used (e.g., fifteen to twenty degrees).

Another knee brace embodiment as disclosed herein may broadly include: an elastic material; a lower hinge retaining member; an upper hinge retaining member; a hinge member; and lower and upper cinching straps.

In this embodiment, a first portion of the elastic material has first and second ends spaced apart a first distance and being fixedly secured together to form a sleeve configured to encircle a leg of the wearer below the knee, to apply a first level of compression thereto; and a second portion of the elastic material has first and second ends spaced apart a second distance, being configured to encircle a leg of the wearer above the knee, to apply a second level of compression thereto.

The lower hinge retaining member is fixedly secured to the first (lower) portion of the elastic material, and includes: an orifice in an upper portion thereof, an opening on a rear portion thereof, and an opening on a forward portion thereof. Similarly, the upper hinge retaining member is fixedly secured to the second (upper) portion of the elastic material, and includes: an orifice in a lower portion thereof, an opening on a rear portion thereof, and an opening on a forward portion thereof.

The hinge member includes: an upper arm, a lower arm, and a polycentric hinge, with the upper arm and the lower arm being moveably coupled with respect to each other using the polycentric hinge. The lower arm is slidably received in the orifice in the upper portion of the lower hinge retaining member; and the upper arm is slidably received in the orifice in the lower portion of the upper hinge retaining member.

A first end of the lower cinching strap may be fixedly secured to the opening on the rear side of the lower hinge retaining member; and a second end of the lower cinching strap is configured to loop around the leg of the wearer and through the opening on the forward side of the lower hinge retaining member, and be releasably secured to itself to cinch the lower hinge retaining member to the leg of the wearer below the knee. Similarly, a first end of the upper cinching strap is fixedly secured to the opening on the rear side of the upper hinge retaining member; and a second end of the upper cinching strap is configured to loop around the leg of the wearer and through the opening on the forward side of the upper hinge retaining member and be releasably secured to itself to cinch the upper hinge retaining member to the leg of the wearer above the knee.

To enable the releasable coupling of the hinge member to the hinge retaining members, the lower arm includes a latch orifice, the upper arm includes a latch orifice, the lower hinge retaining member includes a latch configured to engage the latch orifice in the lower arm to releasably secure the lower arm to the lower hinge retaining member; and the upper hinge retaining member comprises a latch configured to engage the latch orifice in the upper arm to releasably secure the upper arm to the upper hinge retaining member. This releasable securement permits replacement of the hinge member that is currently in use with another hinge member that has different characteristics.

The latch on the lower hinge retaining member may be formed as a cantilevered tab, with a triangular-shaped protrusion having an angled side and a flat side. The angled side is configured to cause deflection of the cantilevered tab when the lower arm is initially inserted into the upper portion of the lower hinge retaining member, until the protrusion is received in the latch orifice of the lower arm; and the flat side of the protrusion configured to engage the lower arm within the latch orifice to releasably latch the lower arm to the lower hinge retaining member.

The latch on the upper hinge retaining member may also be formed as a cantilevered tab, with a triangular-shaped protrusion having a slanted side and a non-slanted side. The slanted side is configured to cause deflection of the cantilevered tab on the upper hinge retaining member when the upper arm is initially inserted into the lower portion of the upper hinge retaining member, until being received in the latch orifice of the upper arm; and the non-slanted side of the protrusion configured to engage the upper arm within the latch orifice of the upper arm to releasably latch the upper arm to the upper hinge retaining member.

Each of the cantilevered tabs may include a protruding lip configured for actuation by the wearer to reposition the tab to release the corresponding arm.

BRIEF DESCRIPTION OF THE DRAWINGS

The description of the various example embodiments is explained in conjunction with appended drawings, in which:

FIG. 1 is a front view of the improved knee brace disclosed herein;

FIG. 2 is a left side view of the knee brace of FIG. 1;

FIG. 3 is a rear view of the knee brace of FIG. 1;

FIG. 4 is a right side view of the knee brace of FIG. 1;

FIG. 6 is the left side view of the knee brace as seen in FIG. 2, but shown enlarged;

FIG. 6A is a cross-sectional view through the upper hinge retaining member, the leg of the polycentric hinge that is releasably retained within an opening therein.

FIG. 12A is a front view of the flexible non-elastic member that is fixedly secured to the upper-outer securement flap;

FIG. 12B is a rear view of the flexible non-elastic member and upper-outer securement flap of FIG. 12A, also showing a piece of hook material fixedly secured to that side of the flexible non-elastic member, and showing the upper inner securement member folded away from the upper outer securement member;

FIG. 12C is a top view of the flexible non-elastic member, the upper-outer securement flap, and the piece of hook material shown in FIG. 12B;

FIG. 12D is the rear view of FIG. 12B, but is shown with the upper inner securement member folded towards the upper outer securement member;

DETAILED DESCRIPTION OF THE INVENTION

Figure 5:
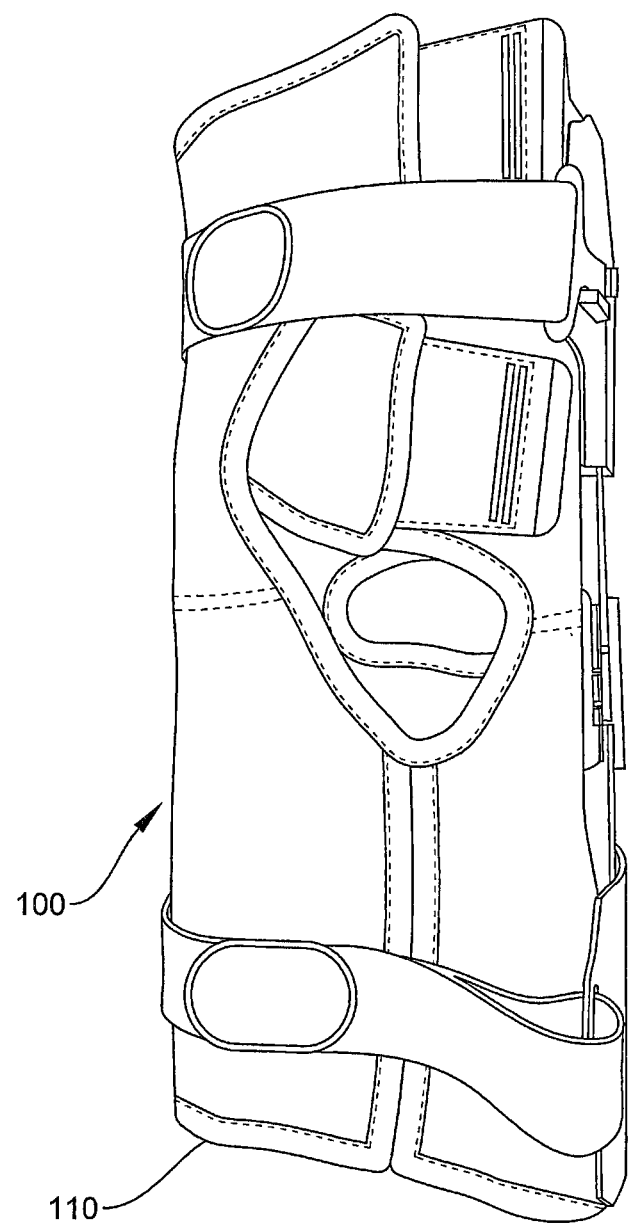
FIG. 5 is the front view of the knee brace as seen in FIG. 1, but shown enlarged.

As used throughout this specification, the word "may" is used in a permissive sense (i.e., meaning having the potential to), rather than a mandatory sense (i.e., meaning must), as more than one embodiment of the invention may be disclosed herein. Similarly, the words "include", "including", and "includes" mean including but not limited to.

The phrases "at least one", "one or more", and "and/or" may be open-ended expressions that are both conjunctive and disjunctive in operation. For example, each of the expressions "at least one of A, B and C", "one or more of A, B, and C", and "A, B, and/or C" herein means all of the following possible combinations: A alone; or B alone; or C alone; or A and B together; or A and C together; or B and C together; or A, B and C together.

Also, the disclosures of all patents, published patent applications, and non-patent literature cited within this document are incorporated herein in their entirety by reference. However, It is noted that the citing of any reference within this disclosure, i.e., any patents, published patent applications, and non-patent literature, is not an admission regarding a determination as to its availability as prior art with respect to the herein disclosed and claimed apparatus/method.

Furthermore, any reference made throughout this specification to "one embodiment" or "an embodiment" means that a particular feature, structure or characteristic described in connection therewith is included in at least that one particular embodiment. Thus, the appearances of the phrases "in one embodiment" or "in an embodiment" in various places throughout this specification are not necessarily all referring to the same embodiment. Therefore, the described features, advantages, and characteristics of any particular aspect of an embodiment disclosed herein may be combined in any suitable manner with any of the other embodiments disclosed herein.

Additionally, any approximating language, as used herein throughout the specification and claims, may be applied to modify any quantitative or qualitative representation that could permissibly vary without resulting in a change in the basic function to which it is related. Accordingly, a value modified by a term such as "about" is not to be limited to the precise value specified, and may include values that differ from the specified value in accordance with applicable case law. Also, in at least some instances, a numerical difference provided by the approximating language may correspond to the precision of an instrument that may be used for measuring the value. A numerical difference provided by the approximating language may also correspond to a manufacturing tolerance associated with production of the aspect/feature being quantified. Furthermore, a numerical difference provided by the approximating language may also correspond to an overall tolerance for the aspect/feature that may be derived from variations resulting from a stack up (i.e., the sum) of a multiplicity of such individual tolerances.

Any use of a friction fit (i.e., an interface fit) between two mating parts described herein indicates that the opening (e.g., a hole) is smaller than the part received therein (e.g., a shaft), which may be a slight interference in one embodiment in the range of 0.0001 inches to 0.0003 inches, or an interference of 0.0003 inches to 0.0007 inches in another embodiment, or an interference of 0.0007 inches to 0.0010 inches in yet another embodiment, or a combination of such ranges. Other values for the interference may also be used in different configurations (see e.g., "Press Fit Engineering and Design Calculator," available at: www.engineersedge.com/calculators/machine-design/press-fit/press-fit-calculator.htm).

Any described use of a clearance fit indicates that the opening (e.g., a hole) is larger than the part received therein (e.g., a shaft), enabling the two parts to move (e.g. to slide and/or rotate) when assembled, where the gap between the opening and the part may depend upon the size of the part and the type of clearance fit—i.e., loose running, free running, easy running, close running, and sliding (e.g., for a 0.1250 inch shaft diameter the opening may be 0.1285 inches for a close running fit, and may be 0.1360 inches for a free running fit; for a 0.5000 inch diameter shaft the opening may be 0.5156 inches for a close running fit and may be 0.5312 inches for a free running fit). Other clearance amounts are used for other clearance types. See "Engineering Fit" at: https://en.wikipedia.org/wiki/Engineering_fit; and "Three General Types of Fit," available at www.mm-to.org/dclark/Reports/Encoder%20Upgrade/fittolerences%20%5BRead-Only%5D.pdf.

The terms "rigid," and "flexible," and "resilient" may be used herein to distinguish characteristics of portions of certain features of the knee brace. Use of the term "rigid" indicates that the described element is devoid of flexibility such that it does not readily lose its overall shape when force is applied, and in fact it may break if an attempt to bend it is made with sufficient force. Use of the term "flexible" indicates that the described element is capable of repeated bending such that it may be bent into different shapes and does not retain a general shape, but instead readily deforms when force is applied. Use of the term "resilient" indicates that the described element has such flexible features and also has a tendency to return to its initial general shape without permanent deformation once a force that causes such flexure is removed. Use of the term "semi-rigid" indicates that the described element may have some degree of flexibility or resiliency.

It noted that this application describes multiple brace embodiment each of which may be configured (e.g., sized/shaped) for use on the wearer's leg as a knee brace, and may also be configured for use on the wearer's arm as an elbow brace. To simplify the following descriptions, those embodiments are referred to throughout this specification as a "knee" brace, without intending the following brace embodiments to be so limited to use on only a patient's leg to support the knee joint, irrespective of certain features that may be particularly directed to aspects of a wearer's knee geometry.

FIGS. 1-4 show front, left side, rear, and right side views of one knee (or elbow) brace embodiment-knee brace 100, which views are shown enlarged within FIGS. 5-8, respectively. The knee brace 100 may be formed of: a particularly shaped elastic material portion 110 (see FIG. 6), a hinge member 130, a lower hinge retaining member 150, an upper hinge retaining member 160, a lower cinching strap 170, and an upper cinching strap 180. Another version of the knee brace 100 may also include a quick-release coupler assembly 190 and corresponding socket.

Note that second and third knee brace embodiments may be similarly formed, with the second embodiment being the same as the first version of knee brace 100 except that it does not include the hinge member 130, the lower hinge retaining member 150, the upper hinge retaining member 160, and the quick-release coupler assembly 190; and with the third embodiment being the same as knee brace 100 except that it does not include the double upper flap arrangement discussed in detail hereinafter, and may merely have a full sleeve over the upper and lower leg portions that accommodates the lower hinge retaining member 150, the upper hinge retaining member 160, and the hinge member 130. These alternate embodiments may be understood from the following description of the full knee brace 100 embodiment that includes all of those features described together in combination.

The elastic material portion 110 utilized for knee brace 100 may be formed of a single piece of the elastic material, or alternatively may be formed of several pieces of the elastic material that may be fixedly secured together similar to the making of a garment of clothing. The elastic material utilized for the elastic material portion 110 may be any suitable natural or synthetic material known in the art of orthotics, including, but not limited to, a neoprene material; a cloth material made of spandex, nylon, bamboo, etc., blends thereof; the orthotic material shown by U.S. Pat. No. 5,735,807 to Cropper; etc.

Figure 7:
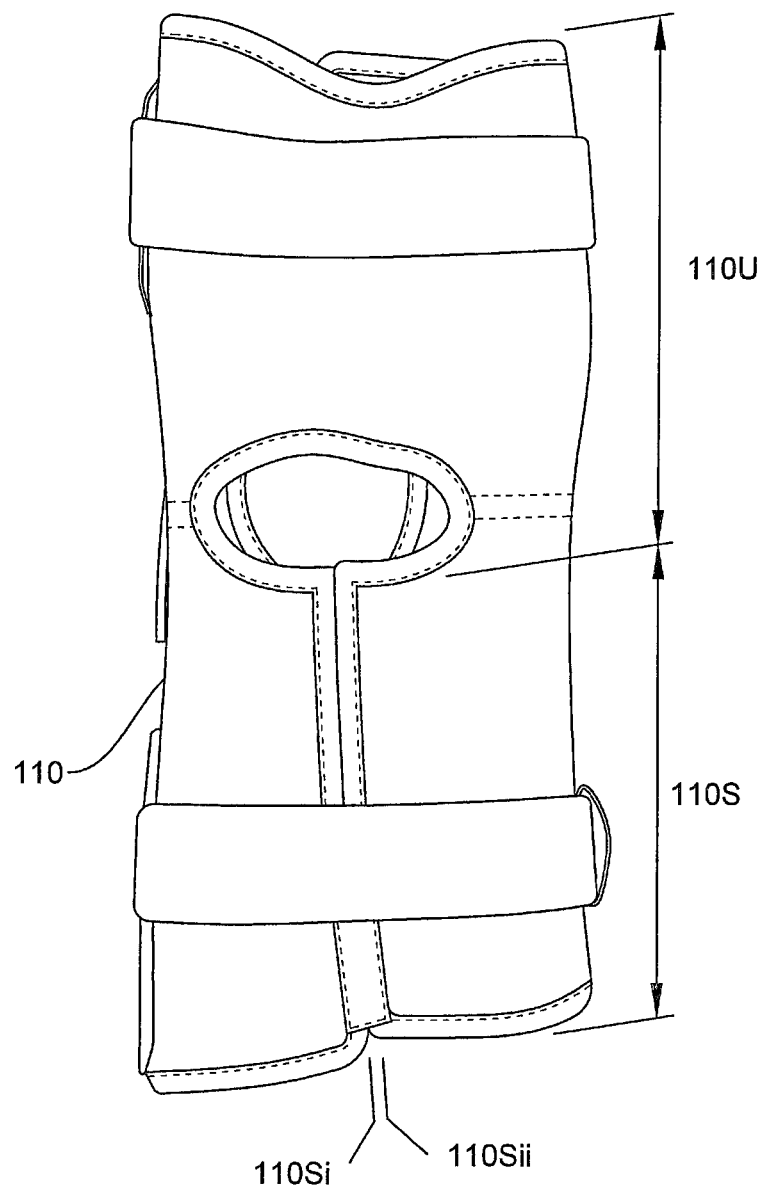
FIG. 7 is the rear view of the knee brace as seen in FIG. 3, but shown enlarged.
Figure 8:
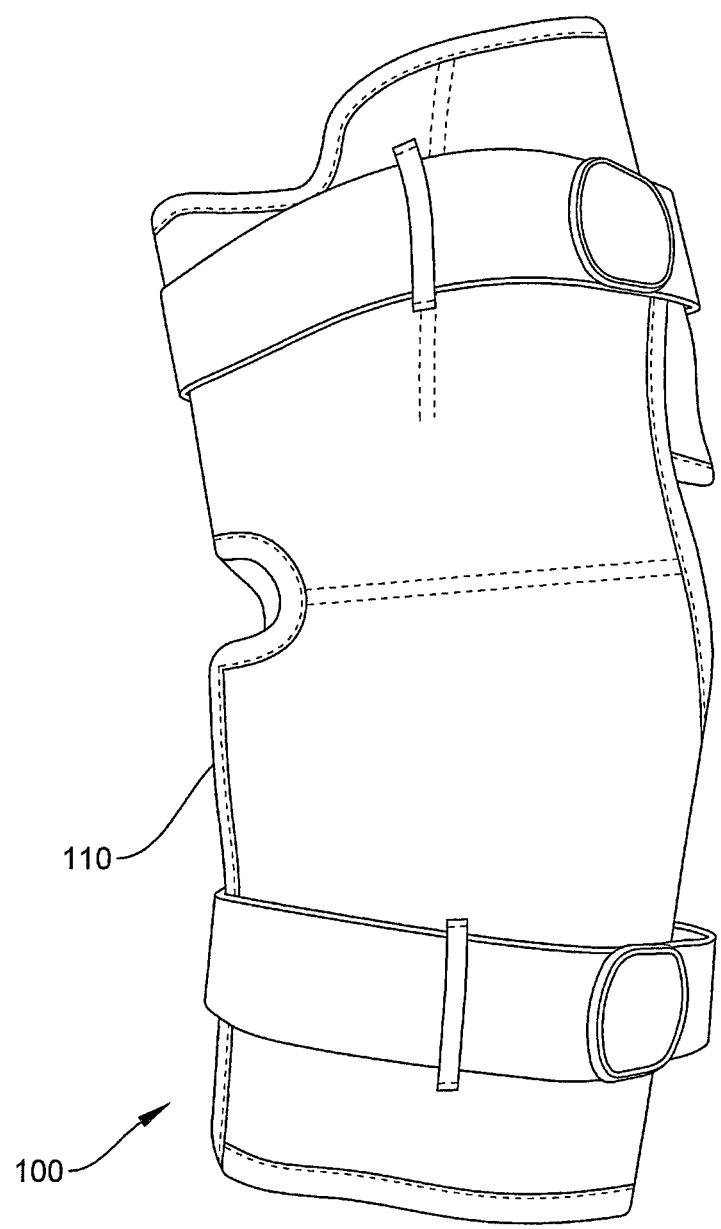
FIG. 8 is the right side view of the knee brace as seen in FIG. 4, but shown enlarged.
Figure 12:
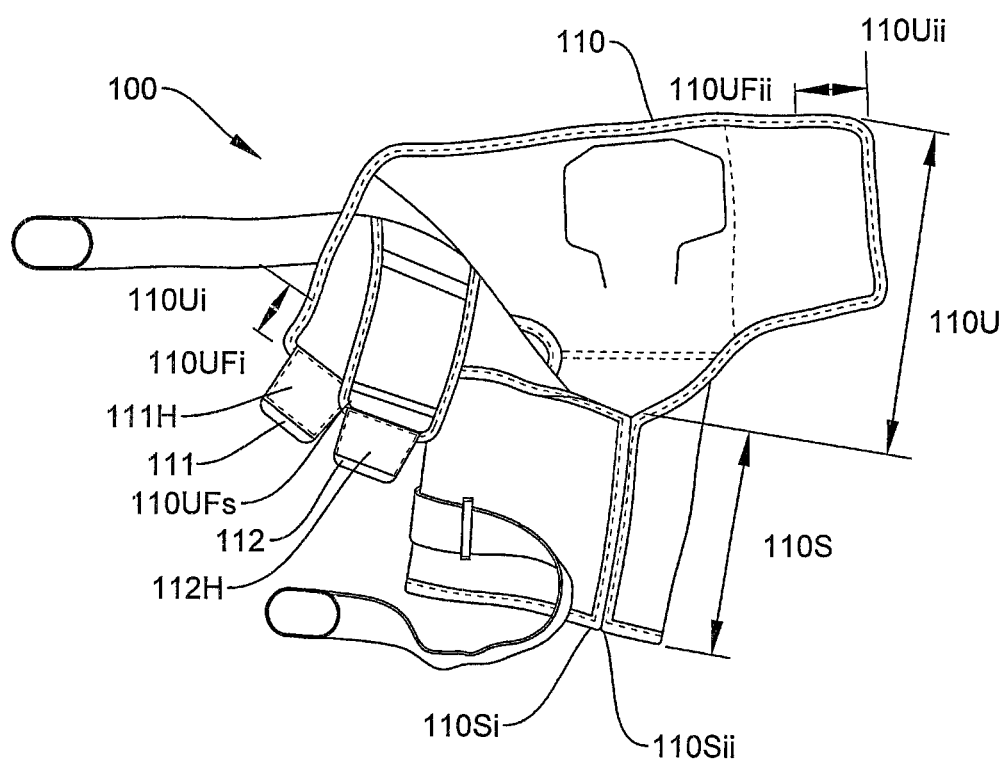
FIG. 12 is the view of FIG. 11, but shown with the upper, inner securement flap also detached from the opposing upper flap member, and with both the upper outer and inner flaps folded back away from the opposing flap member, and with the opposing flap unfolded away from the upper-outer and upper-inner flaps.

The elastic material portion 110, as may be seen in FIG. 7 and FIG. 12, may generally have its lengthwise ends 110Si and 110Sii for the lower portion be wrapped around and be fixedly secured to each other (e.g., by stitching) to form a lower sleeve portion 110S. This lower sleeve portion 110S may be sized and shaped to encircle the wearer's leg below the knee (e.g., to encircle at least portions of the lower calf, the mid-calf, and/or upper calf muscle of the wearer's leg).

The upper part 110U of the elastic material portion 110 may be formed with material utilized between its ends 110Ui and 110Uii having a longer length than the length of material used between the ends 110Si and 110Sii. The longer length between the ends 110Ui and 110Uii enable forming the upper portion 110U with a sufficient amount of material so that it may not only circumscribe the thigh of the wearer, which is generally larger than the calf region of the leg, but to also has extra material on each side that forms a first flap 110UFi and a second flap 110UFii (see FIG. 12). With the upper portion 110U properly positioned on the thigh of the wearer, the first flap 110UFi and a second flap 110UFii overlap each other, and with the first flap 110UFi angled upwardly (i.e., angle Cup) with respect to a traverse plane (i.e., being a plane that cuts the body into top and bottom portions)—see FIG. 14. As seen in FIG. 12 and FIGS. 12B and 12D, the secondary flap 110UFs may be fixedly secured to the inside (or also on the outside) of the upper portion 110U, being adjacent to, but angled downwardly with respect to the first flap 110UFi, at an acute angle θ. The interior sides of each of the first flap 110UFi and secondary flap 110UFs may be formed with either a piece of hook type material or the corresponding loop type material to which it may be attached-which hook and loop materials are descriptive names for such materials that are sold under the trademark VELCRO®, while the exterior side of the second flap 110UFii may be formed with a piece of the other of those two materials. For example, the interior side of each of the first flap 110UFi and secondary flap 110UFs may be formed with a piece of the hook type material, while the exterior side of the second flap 110UFii may be formed with a piece 110UFL of the loop type material (see FIG. 12). Thus, the secondary flap 110UFs may be secured to the second flap 110UFii to be angled downwardly (i.e., angle (down) with respect to a traverse plane.

The first flap 110UFi being angled upwardly (i.e., angle Cup) with respect to a traverse plane, and the secondary flap 110UFs being angled downwardly (i.e., angle @down) with respect to a traverse plane, may each be an angle that is in the range of five degree to eight degrees in one embodiment, and may be an angle that is in the range of eight degree to twelve degrees in another embodiment, and may be an angle that is in the range of twelve degree to fifteen degrees in yet another embodiment, and may be a combination of such ranges of angles or other ranges of angles may be used in other embodiments. The divergence between the axial direction of the two flaps permits tensioning of the first flap 110UFi in a first direction and tensioning of the secondary flap 110UFs in a second direction, being at the angle with respect to each other (i.e., angle $\alpha_{up}$+angle $\alpha_{down}$), which allows for more stable securement of the brace to the thigh of the wearer to better prevent downward migration of the brace 100.

Being so configured, the lower sleeve portion 110S that encircles the leg below the knee may be sized to apply a first level of compression thereto; the first flap 110UFi releasably secured to the second flap 110UFii of the upper portion 110U that encircles an upper portion of the thigh of the wearer may be cinched to apply a second level of compression thereto; and the secondary flap 110UFs releasably secured to the second flap 110UFii that encircles a lower portion of the thigh of the wearer may be cinched to apply a third level of compression thereto. The second and third levels of compression may be the same, but are preferably higher than the first level of compression, to better maintain the brace at the proper position, in addition to the strap arrangement.

To provide better support for the piece(s) of hook material, and to permit easier coupling of the ends of the upper portion 110U about the thigh of the wearer, a flexible non-elastic member (e.g., a flexible non-elastic rubber or plastic) may be fixedly secured (e.g., stitched) to the distal end of each of the first flap 110UFi and secondary flap 110UFs, respectively. As seen in FIGS. 12A-12D, a flexible non-elastic member 111 may be fixedly secured to the end 110Ui of the first flap 110UFi, and a flexible non-elastic member 112 may be fixedly secured to the distal free end of the secondary flap 110UFs. The inwardly facing side of the flexible non-elastic member 111 that is fixedly secured to the first flap 110UFi may have a piece 111H of the hook material fixedly secured thereto (e.g., using stitching 113), and the inwardly facing side of the flexible non-elastic member 112 that is fixedly secured to the first flap 110UFi may have a piece 112H of the hook material fixedly secured thereto. The ends of the pieces of hook materials 111H and 112H are preferably positioned a small amount from the distal ends of the respective flexible non-elastic members 111 and 112 (see FIG. 12C), and the distal ends of the respective flexible non-elastic members 111 and 112 are preferably formed with a bulbous shape that protrudes to the outer side (e.g., the triangular shape shown in FIG. 12C), both of which features better enable a wearer of the brace 100 to grasp the end of the flexible non-elastic members when securing and unsecuring those flaps. It may be much easier to grasp the end of the flexible non-elastic members because of the thickness and shape of the protrusion, and because that distal end portion being without the hook material will not be secured to, and thus not be maintained in close contact with, the loop type material on the exterior side of the second flap 110UFii. In fact, the distal end portion of the flexible non-elastic members may protrude a small amount tangentially away from the distal point of contact of the hook material.

As shown in FIG. 12D, the acute angle θ at which the secondary flap 110UFs may be angled with respect to the first flap 110UFi, is preferably in the range of 10 degrees to 30 degrees, and more preferably in the range of 15 degrees to 25 degrees, and most preferably in the range of 17 degrees to 23 degrees.

Figure 18:
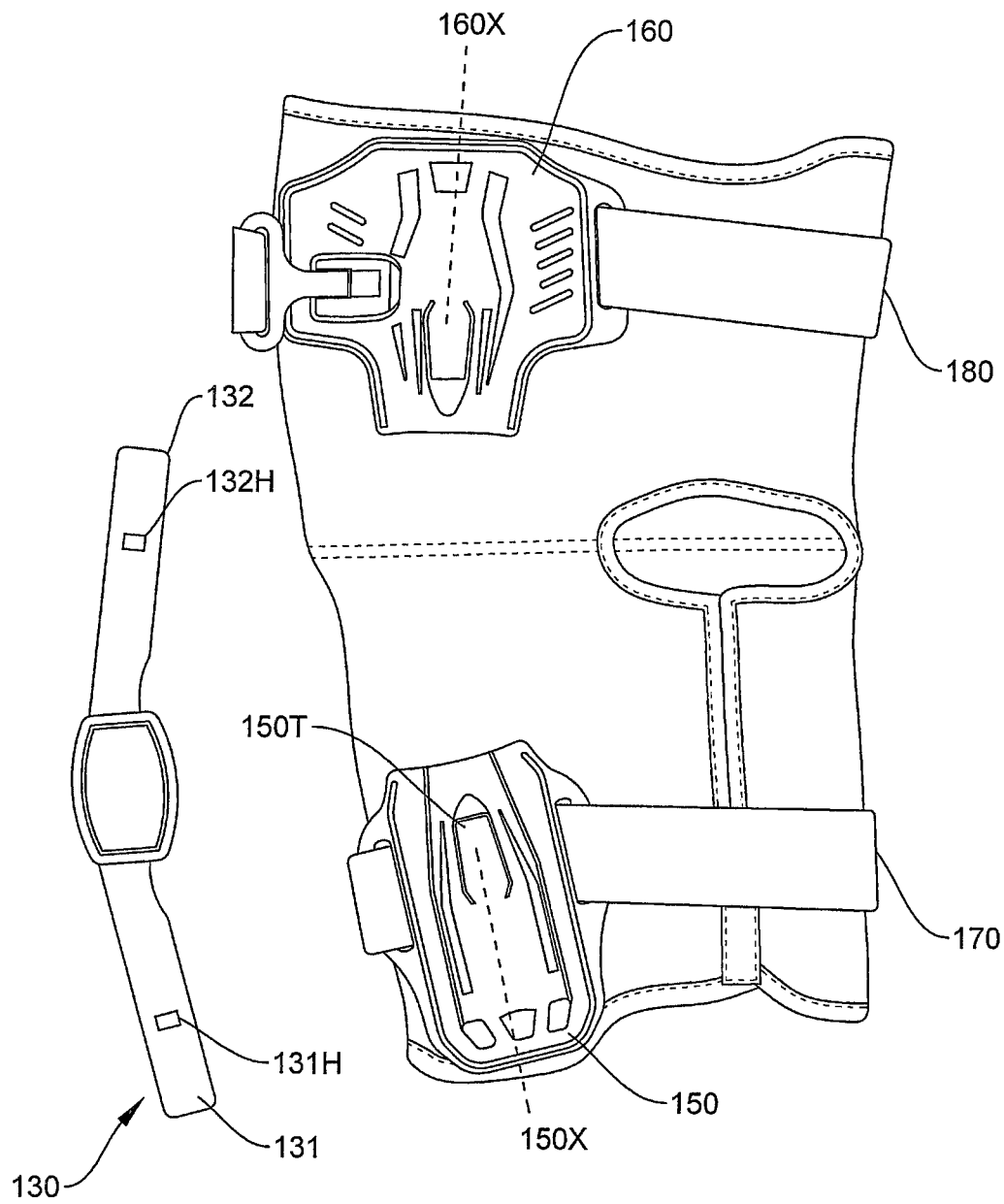
FIG. 18 is the left rear side view of the knee brace of FIG. 1, but is shown with the hinge removed from each of the upper and lower hinge retaining members using the quick-release tabs formed on each.
Figure 22:
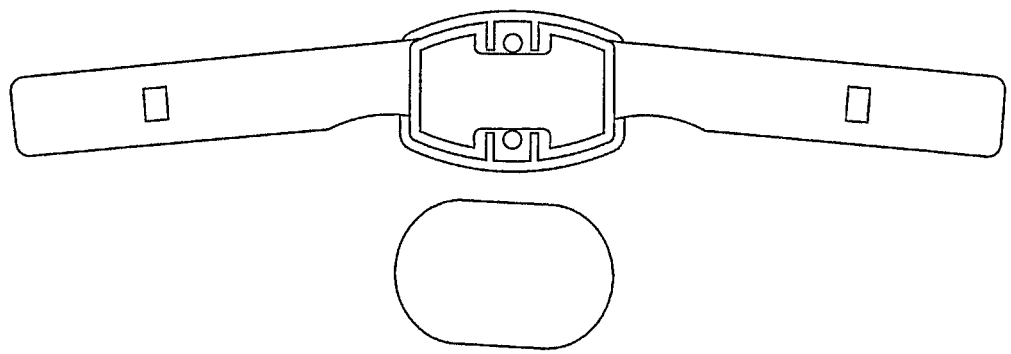
FIG. 22 is the rear view of the bicentric hinge as seen in FIG. 21, but is shown with a pad decoupled from the side of the hinge.
Figure 21:
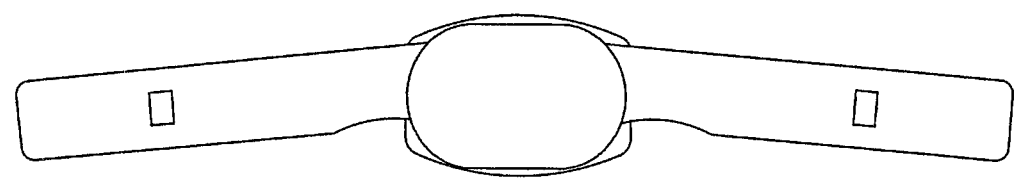
FIG. 21 is a rear view of the bicentric hinge of FIG. 19.
Figure 20:
FIG. 20 is a side view of the bicentric hinge of FIG. 19.
Figure 19:
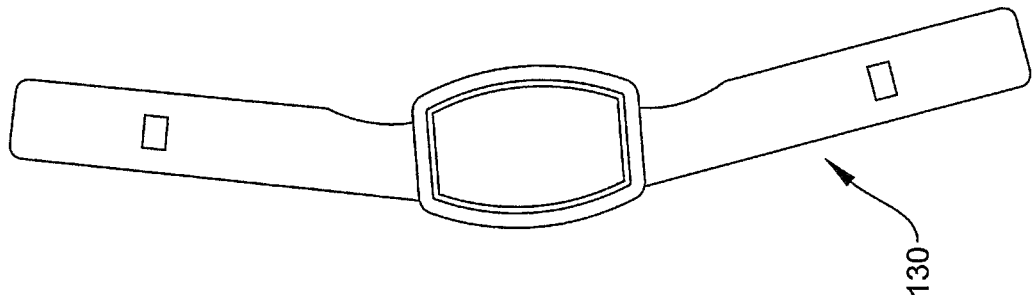
FIG. 19 is a front view of the bicentric hinge used for the knee brace of FIG. 1.
Figure 23:
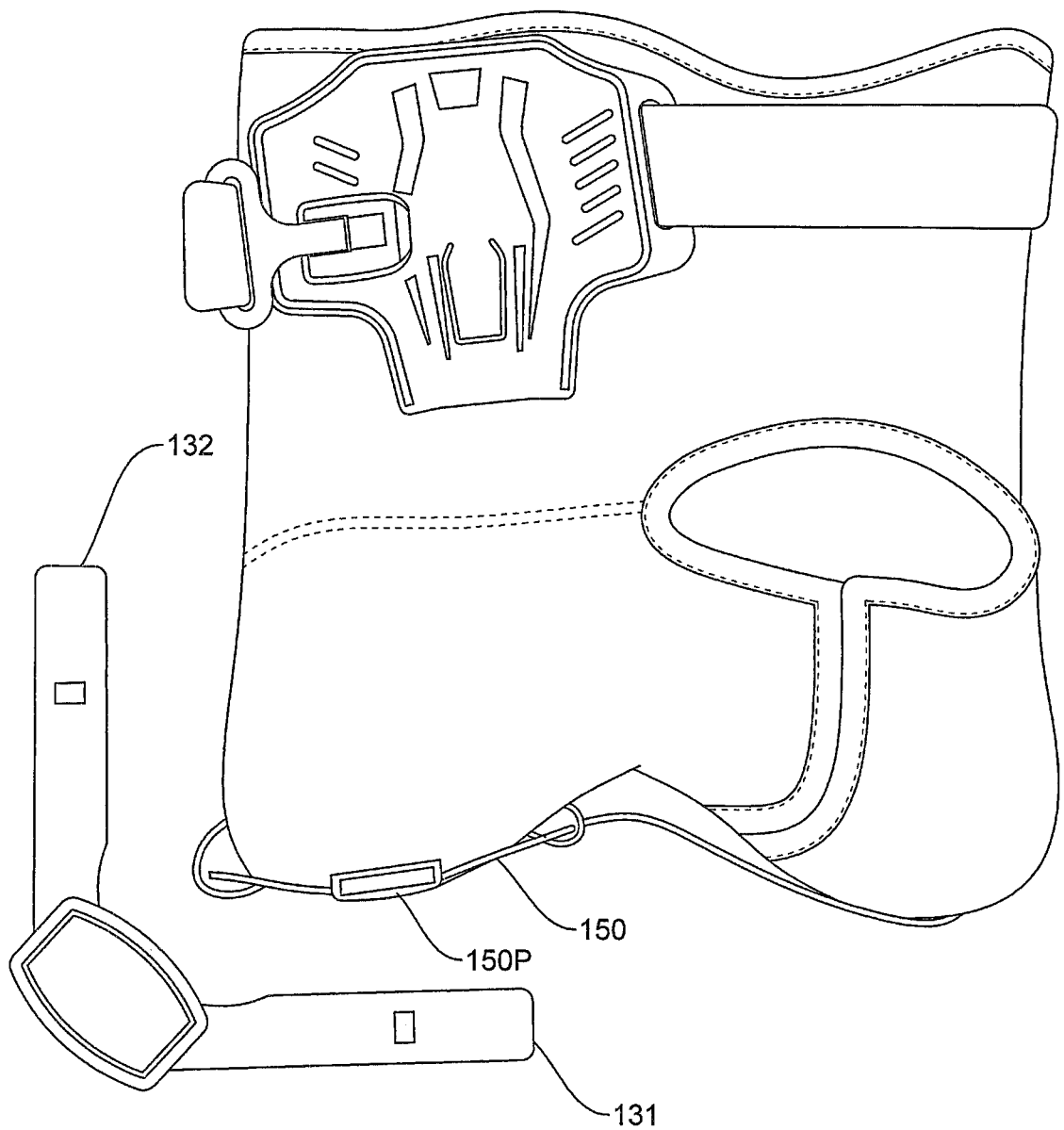
FIG. 23 is the left side view of the brace with the hinge removed, as seen in FIG. 18, but with the lower portion of the sleeve folded laterally into the page to expose the opening in the lower hinge retaining member that receives the lower end of the hinge.
Figure 24:
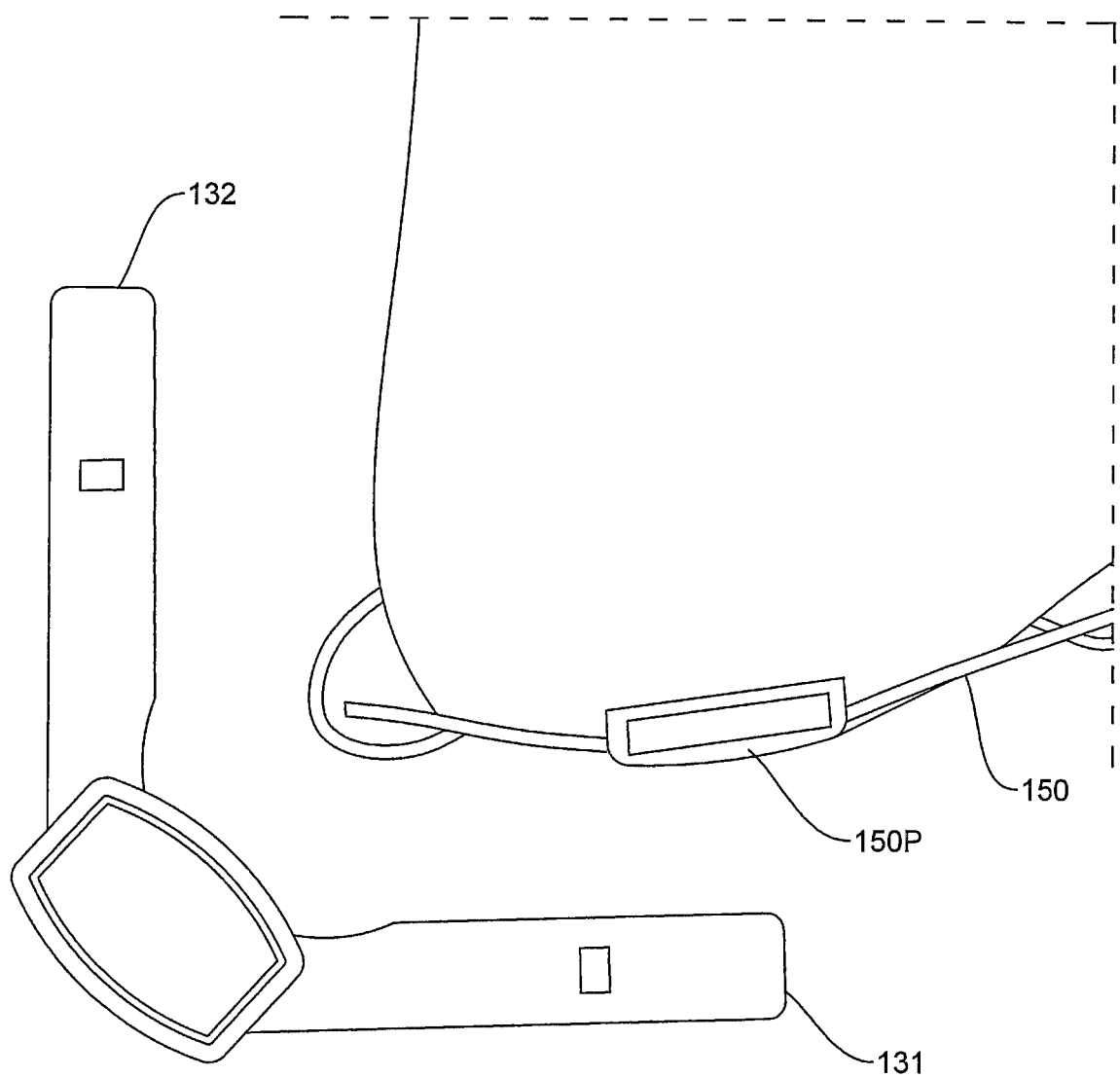
FIG. 24 is the left side view of FIG. 23, but shown enlarged.

The lower hinge retaining member 150 and upper hinge retaining member 160 (FIG. 18) may each be made of any suitable material, including, but not limited to, a plastic material, a thermoplastic elastomer, etc. As seen in FIGS. 23-24, the lower hinge retaining member 150 and upper hinge retaining member 160 may each be made sufficiently thick proximate to its center, with the thickness extending in the respective axial directions 150X and 160X, to be able to form an opening in each retaining member (e.g., opening 150P in member 150), which openings in the two retaining members may respectively receive a portion of the arms 131 and 132 of the hinge member 130. The arms 131 and 132 of the polycentric hinge 130 may have a rectangular cross-sectional shape, and the openings in the hinge retaining members 150 and 160 may be correspondingly shaped. Latching orifices 131H and 132H may be respectively formed in the arms 131 and 132 of the polycentric hinge 130, and a three-sided slot may be formed in each of the lower hinge retaining member 150 and upper hinge retaining member 160 to interconnect with the openings (e.g., opening 150P in member 150) to form cantilevered quick release tabs 150T and 160T, which cantilevered tabs may have an inward facing protrusion configured to engage those orifices when the arms 150/160 are inserted into the openings in the retaining members (see FIG. 6A). The protrusion may be triangular-shaped, having an angled surface on one side to permit insertion of the hinge arm by deflecting the tab(s) outwardly, and may have a flat surface (i.e., being generally perpendicular to the tab) on the other side to bear against an inner side of the respective latching orifices 131H and 132H when captured therein. The tabs may have a protruding lip that may be grasped to actuate the tabs to release the arms of the hinge member, permitting its replacement with a different hinge member 130 that may possess different characteristics (e.g., a hinge member with a different hinge arrangement where the arms may pivot at a greater distance away from each other; or a hinge member with a polycentric hinge that has fixed stop locations; or a hinge member with a polycentric hinge that has adjustable stops-see e.g., U.S. Pat. No. 5,443,444 to Pruyssers for "Orthopaedic Polycentric Hinge"; or a hinge member with a polycentric hinge that has a variable axis-see e.g., U.S. Pat. No. 4,699,128 to Aaserude for "Polycentric Variable Axis Hinge"; or any one of the hinges shown by U.S. Pat. No.: 58,403 to Goodwin; U.S. Pat. No. 1,257,297 to Brown; U.S. Pat. No. 3,826,251 to Ross; U.S. Pat. No. 4,520,804 to DiGeorge; U.S. Pat. No. 4,604,770 to Lang; U.S. Pat. No. 4,738,252 to Friddle; U.S. Pat. No. 4,817,588 to Bledsoe; U.S. Pat. No. 4,846,842 to Connolly; U.S. Pat. No. 4,982,732 to Morris; U.S. Pat. No. 5,000,169 to Swicegood; U.S. Pat. No. 5,062,858 to Broeck; U.S. Pat. No. 5,188,584 to Petrofsky; U.S. Pat. No. 5,407,420 to Bastyr; U.S. Pat. No. 5,409,449 to Nebolon; U.S. Pat. No. 5,460,599 to Mahoney; U.S. Pat. No. 5,672,152 to Mason; U.S. Pat. No. 5,814,000 to Kilbey; U.S. Pat. No. 5,873,847 to Bennett; U.S. Pat. No. 5,938,629 to Bloedau; U.S. Pat. No. 5,997,493 to Young; U.S. Pat. No. 6,203,511 to Johnson; U.S. Pat. No. 6,993,808 to Bennett; U.S. Pat. No. 7,235,059 to Mason; U.S. Pat. No. 7,984,531 to Moore; U.S. Pat. No. 8,104,141 to Yamashita; U.S. Pat. No. 8,172,781 to Oddou; U.S. Pat. No. 8,591,444 to Bejarano; U.S. Pat. No. 8,728,018 to McCune; and U.S. Pat. No. 9,458,878 to Scatassa).

The lower hinge retaining member 150 and upper hinge retaining member 160 may each be fixedly secured to the lower sleeve portion 110S and the upper part 110U of the elastic material portion 110, respectively, in any suitable manner, including, but not limited to, being stitched thereto.

The lower hinge retaining member 150 may be formed to thin in each of the lateral directions in moving away from away the axis 150X to the forward and rear ends, which may permit those distal ends to deform and match the contour of the wearer's thigh when the brace 100 is secured thereto. The upper hinge retaining member 160 may similarly be formed to thin in each of the lateral directions in moving away from away the axis 160X to its forward and rear ends.

The lower hinge retaining member 150 and upper hinge retaining member 160 may each be configured to support attachment of the above-noted lower cinching strap 170 and upper cinching strap 180. One end of each strap is fixedly secured to one side of the respective retaining member, and after the straps loop around the calf and thigh of the wearer's leg respectively, the second end of each strap is releasably coupled to the other side of the respective retaining member.

The cinching straps 170 and 180 may be fixedly secured to the retaining member using any method of such attachment known in the art, including, but not limited to, using stitching, mechanical fasteners, etc.

Figure 9:
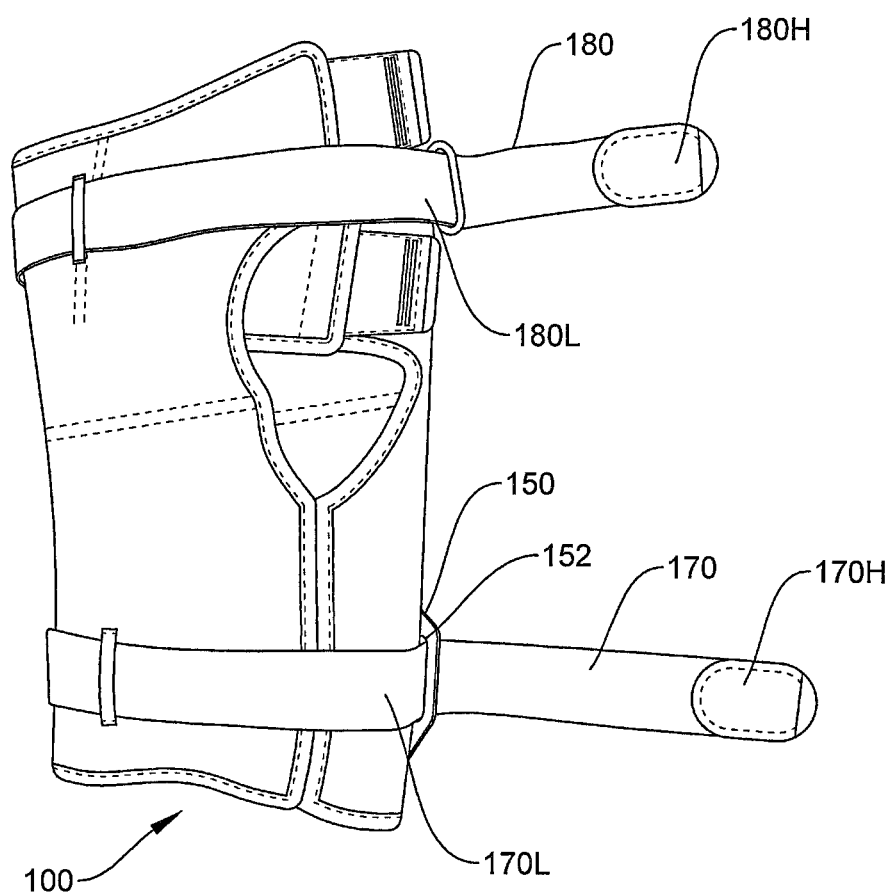
FIG. 9 is a view of the front, right side of the knee brace of FIG. 1, shown with the ends of the upper and lower cinching straps that wrap around the posterior of the brace respectively detached from themselves, but with each still passing through the respective cinching loop.
Figure 10:
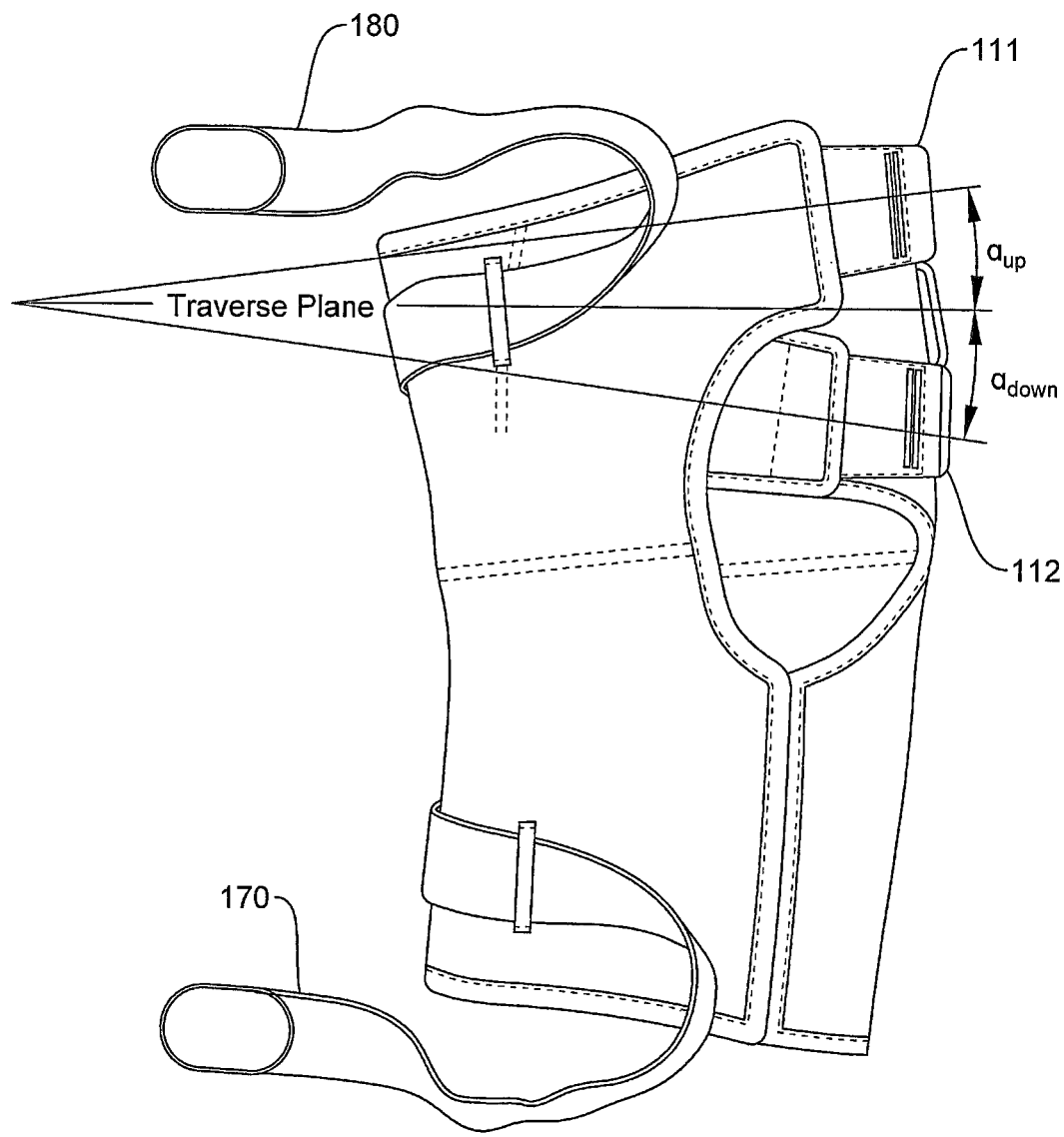
FIG. 10 is the view of FIG. 9, but shown with each of the upper and lower cinching straps withdrawn from the respective cinching loops and folded back away from the front of the brace.
Figure 11:
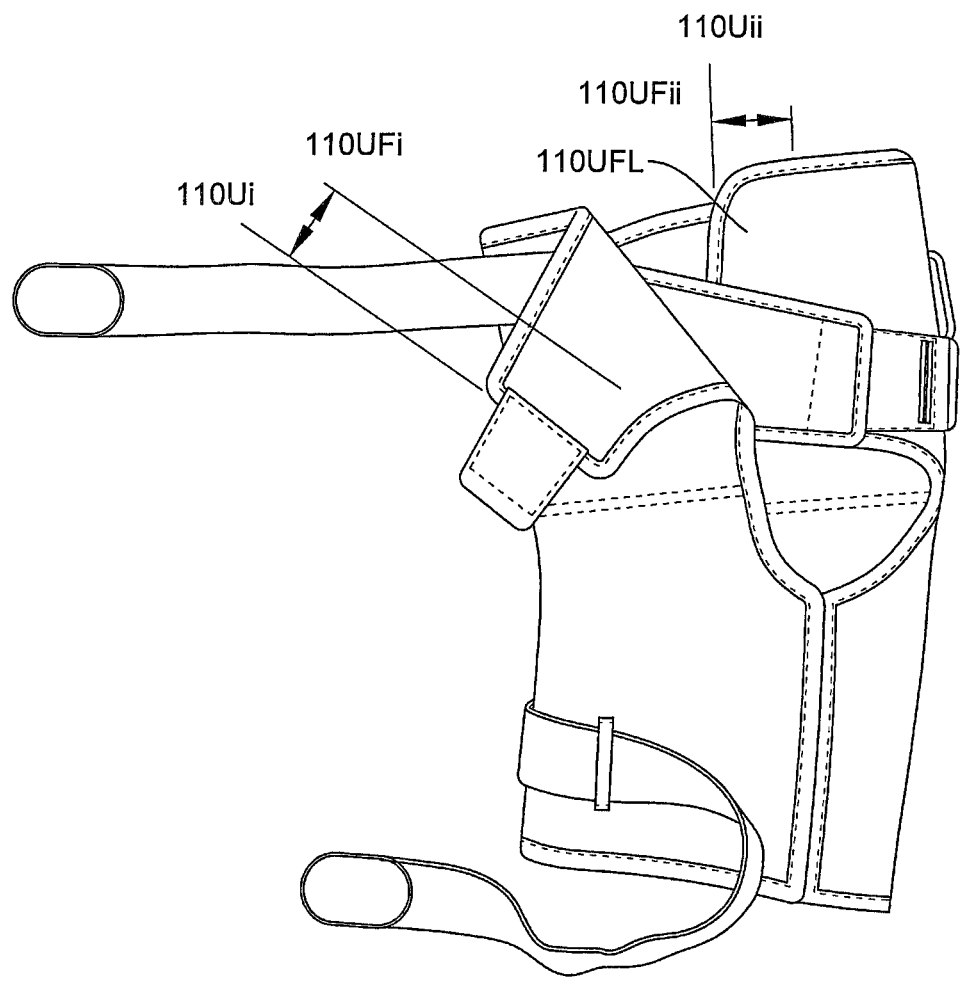
FIG. 11 is the view of FIG. 10, but shown with the upper-outer securement flap detached from the opposing upper flap member.

In one embodiment, the lower hinge retaining member 150 may have a first narrow opening 151 formed at the rear side, so that the cinching strap 170 may loop around the end of the retaining member through the opening 151 and be stitched to itself to be fixedly secured thereto. A second narrow opening 152 may be formed at the front side of the lower hinge retaining member 150. The free end of the strap 170 may have hook type material 170H secured to one side, and may be formed with loop type material 170L on the other side. The cinching strap 170 may be looped around the lower leg of the wearer and be fed through the second narrow opening 152 of the lower hinge retaining member 150 and may be pulled away from the retaining member in the opposite direction to cinch the strap around the calf of the wearer, after which the free end of the strap may be releasably secured to itself using the hook and loop materials 170H and 170L (see FIGS. 10, 9, and 8).

The upper cinching strap 180 may be similarly formed with hook and loop materials 180H and 180L, and the upper hinge retaining member 160 may be similarly formed with narrow forward and rear openings, for the upper cinching strap to releasably secure about the thigh of the wearer of brace 100 in the same manner.

Figure 14:
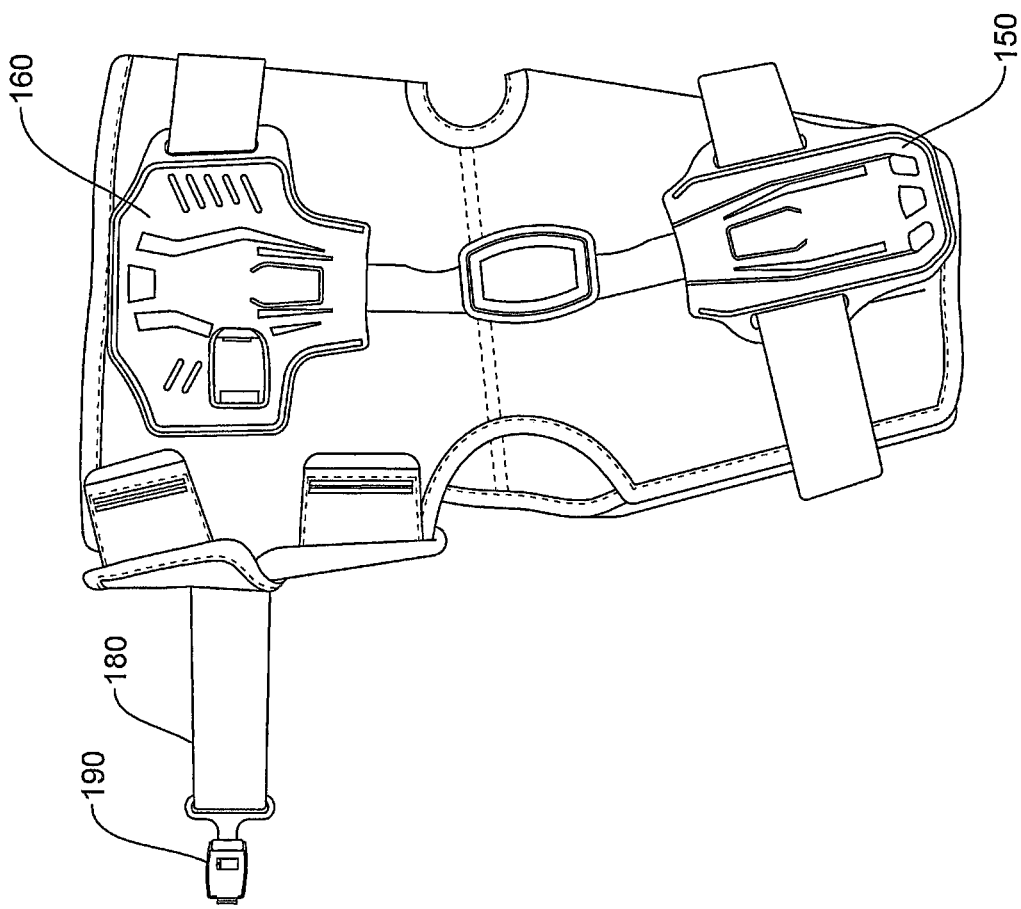
FIG. 13 and FIG. 14 show the left side of the knee brace of FIG. 1, with the quick release coupler joined to the cinching loop of the upper cinching strap being respectively shown when coupled to, and when decoupled from, the socket formed in the upper hinge retaining member.
Figure 13:
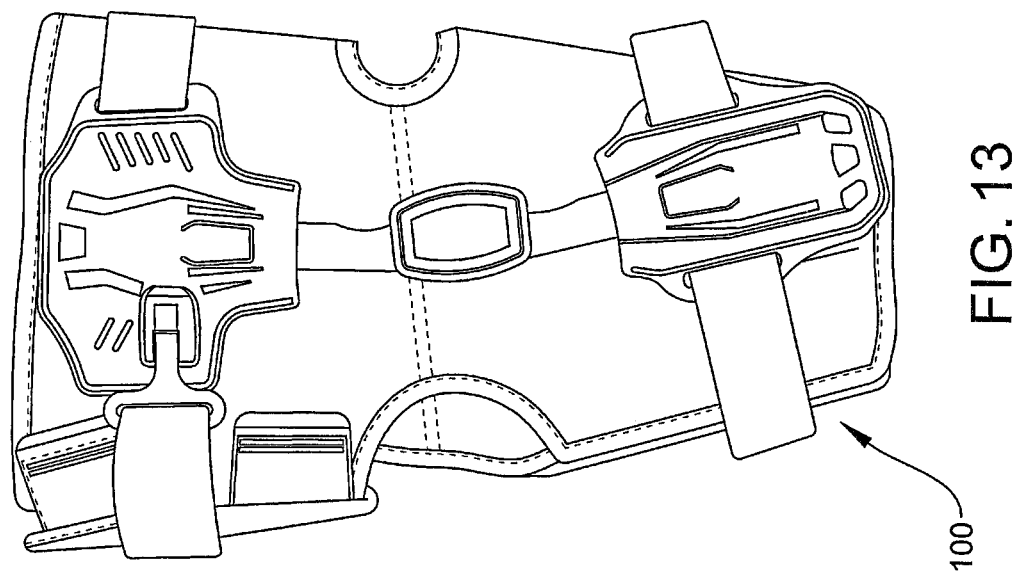
Figure 15:
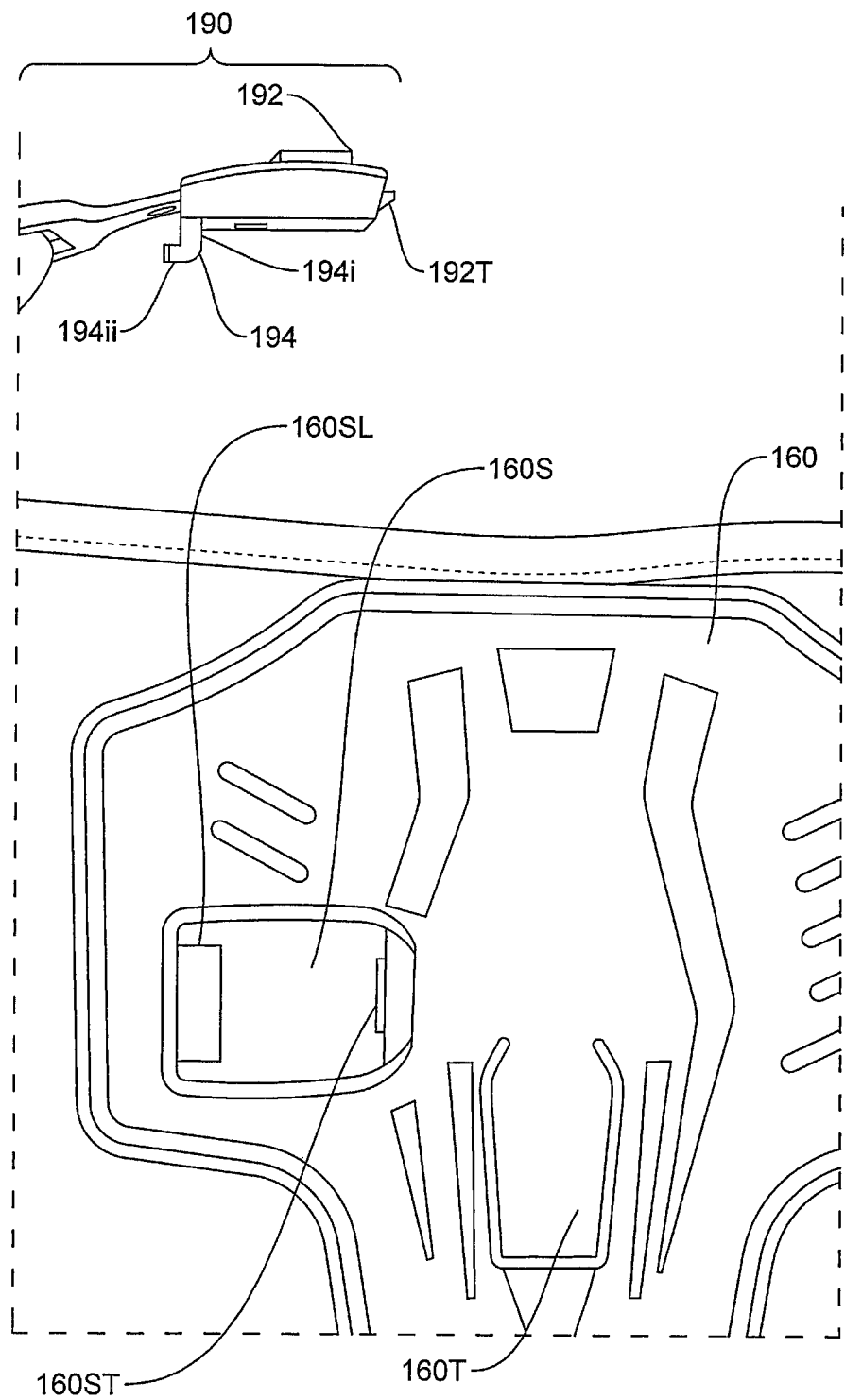
FIG. 15 is the view of FIG. 14, but shown enlarged and with the coupler of the strap turned sideways with respect to the corresponding socket formed in the upper hinge retaining member.
Figure 16:
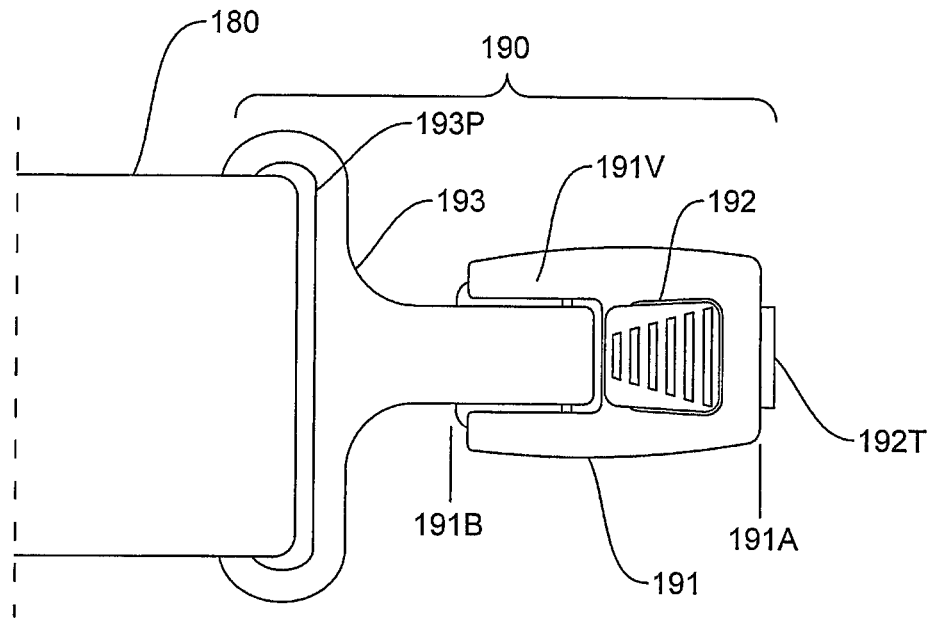
FIG. 16 is an enlarged detail view of the front of the coupler shown in FIG. 15.
Figure 17:
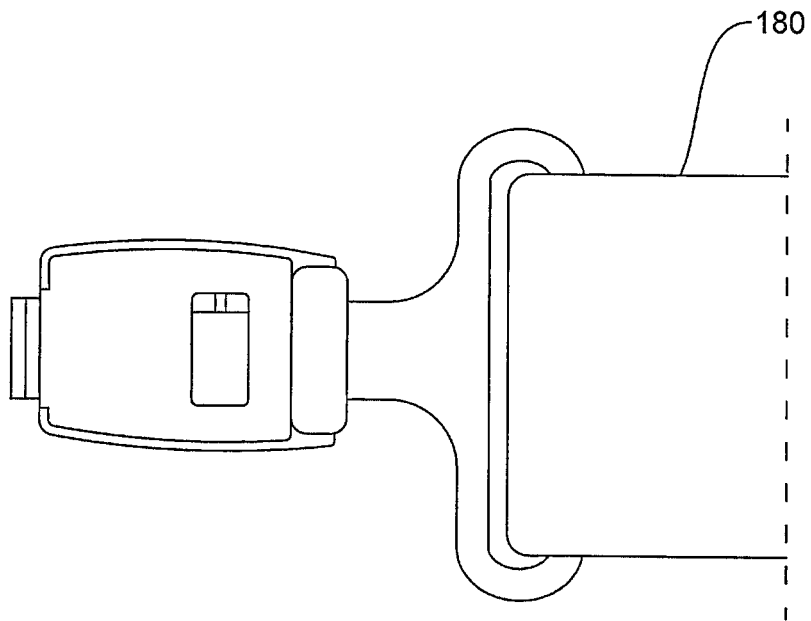
FIG. 17 is an enlarged detail view of the rear of the coupler shown in FIG. 15.

In another embodiment, as seen in FIG. 6 and FIGS. 13-14, the upper hinge retaining member 160 may be formed with only a rear opening 161, to which one end of the upper cinching strap 180 may be fixedly secured, and the free end of the strap may be looped through an opening in the quick-release coupler assembly 190, which assembly may be releasably secured in a socket 160S in the upper hinge retaining member 160. Front and rear views of the quick release coupler 190 are shown in FIGS. 16-17, and the quick-release coupler assembly 190 is shown enlarged and turned sideways in FIG. 15 with respect to the mating socket 160S.

The quick-release coupler assembly 190 may have a housing 191, and a button 192 that is slidably mounted within said housing and biased by a spring (not shown) for a tongue portion 192T of the button to normally protrude out from a first end 191A of the housing. A loop member 193 may be pivotally coupled to the housing 191 at 191V, between its first end 191A and its second end 191B. An opening 193P in the loop member 193 permits the upper cinching strap 180 to loop therethrough before being releasably secured to itself. The housing 191 may also be formed with an L-shaped protrusion 194, which may have a first leg 194i and a second leg 194ii.

The socket 160S may be formed with a corresponding L-shaped recess 160SL configured to receive the L-shaped protrusion 194 of the housing 191, and a transverse recess 160ST configured to receive the tongue portion 192T of the button when the button is biased by the spring into the extended (protruding) position.

When the brace 100 is being applied to the leg of the wearer, to properly secure the upper portion 110U of the brace 100 to the thigh of the wearer, prior to cinching of the upper cinching strap 180 as described above, the first flap 110UFi and the secondary flap 110UFs of the upper portion 110U are releasably secured to the second flap 110UFii.

An opening 110F may be formed in the front to receive the knee cap therein, and an opening 110R may be formed in the rear of the brace, to eliminate bunching of the elastic material portion 110, when the wearer may bend down, which bunching of the elastic material thereat would otherwise tend to restrictive such bending at the knee.

FIGS. 25-33 show various views of another knee (or elbow) brace embodiment-knee/elbow brace 200. The brace 200 may be formed of: a sleeve assembly 205 (see FIG. 28), and a hinge member 230. The sleeve assembly 205 may be formed of: a particularly shaped elastic material portion 210, an upper cinching strap 270, and a lower cinching strap 280.

The elastic material portion 210 of the sleeve may be formed substantially similar to the elastic material portion 110 of brace 100, except for a couple of differences.

Figures 25, 26:
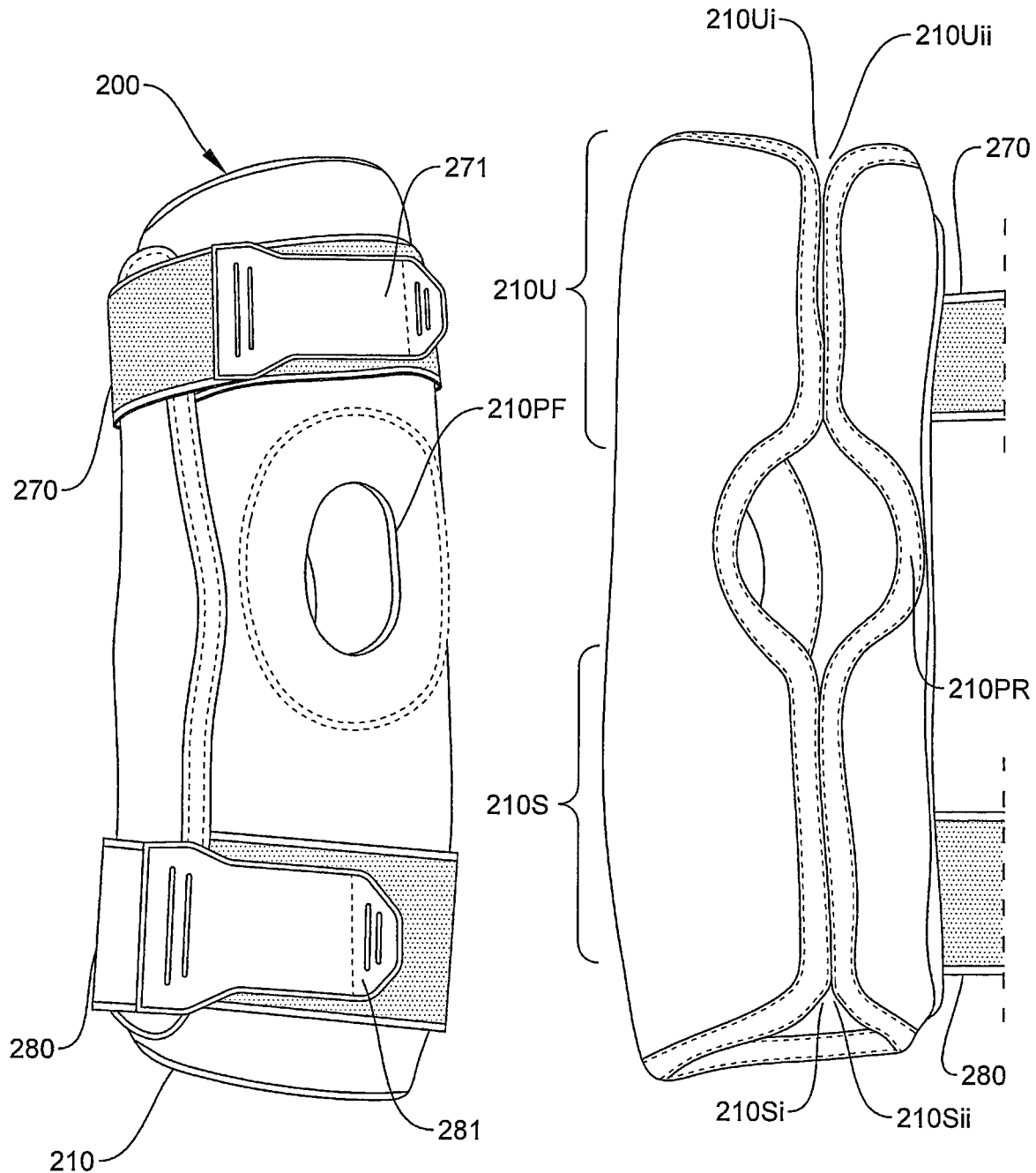
FIG. 25 is a front perspective view of another embodiment of a knee/elbow brace.
FIG. 26 is a rear perspective view of the knee/elbow brace of FIG. 25.

The elastic material portion 210, as may be seen in FIG. 26, may generally have its lengthwise ends 210Si and 210Sii be wrapped around and be fixedly secured to each other (e.g., by stitching) to form a lower sleeve portion 210S. This lower sleeve portion 210S may be sized and shaped to encircle the smaller portion of the wearer's limb on one side of the joint (e.g., to encircle at least a portion of the forearm when used as an elbow brace, or to encircle portions of the lower calf, the mid-calf, and/or upper calf muscle when used as a knee brace).

The upper portion 210U of the elastic material portion 210 may be formed with material utilized between its ends 210Ui and 210Uii having a longer length than the length of material used between the ends 210Si and 210Sii. The upper sleeve portion 210U may be sized and shaped to encircle the larger portion of the wearer's limb on the other side of the joint (e.g., to encircle at least a portion of the upper arm when used as an elbow brace, or to encircle portions of the thigh muscle when used as a knee brace). An opening 210PF may be formed in the front of the elastic material portion 210 to surround the joint (knee or elbow). An opening 210PR may also be formed in the rear of the elastic material portion 210 to prevent bunching when the limb is bent at the joint.

Being so configured, the lower sleeve portion 210S that encircles the limb below the elbow/knee joint may be sized to apply a first level of compression thereto; and the upper sleeve portion 210U that encircles an upper portion of the limb of the wearer above the elbow/knee joint may be sized to apply a second level of compression thereto, which may be greater than the first level of compression.

Figure 27:
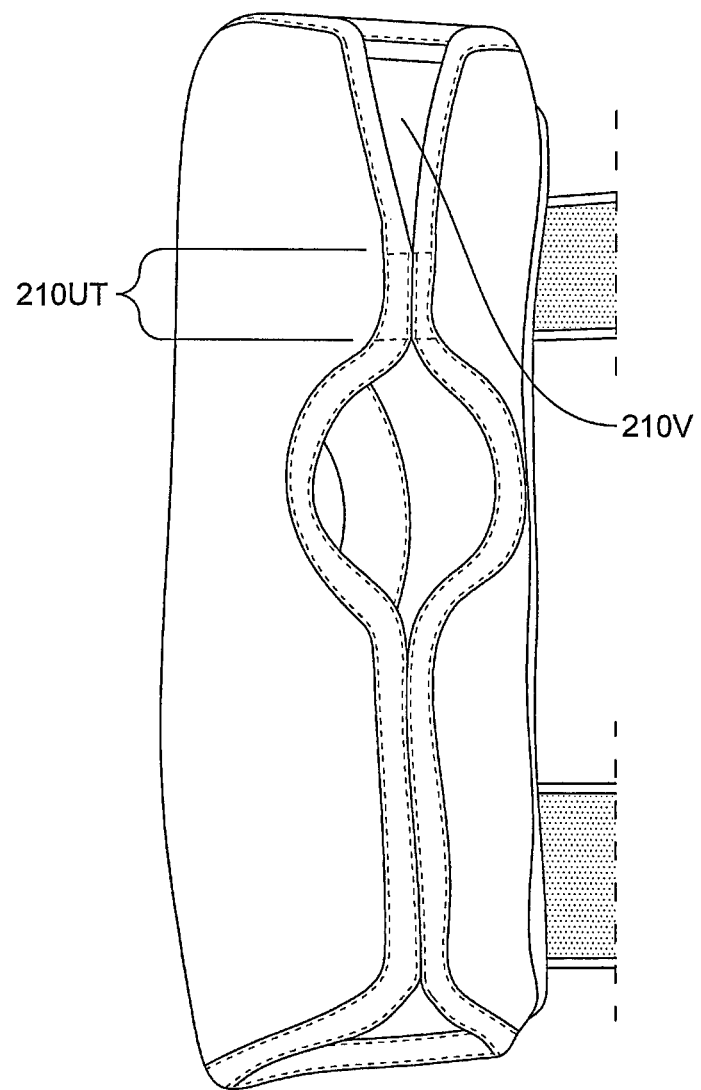
FIG. 27 is a second rear perspective view of the knee/elbow brace of FIG. 25, showing the separable portion at one end of the sleeve.
Figure 28:
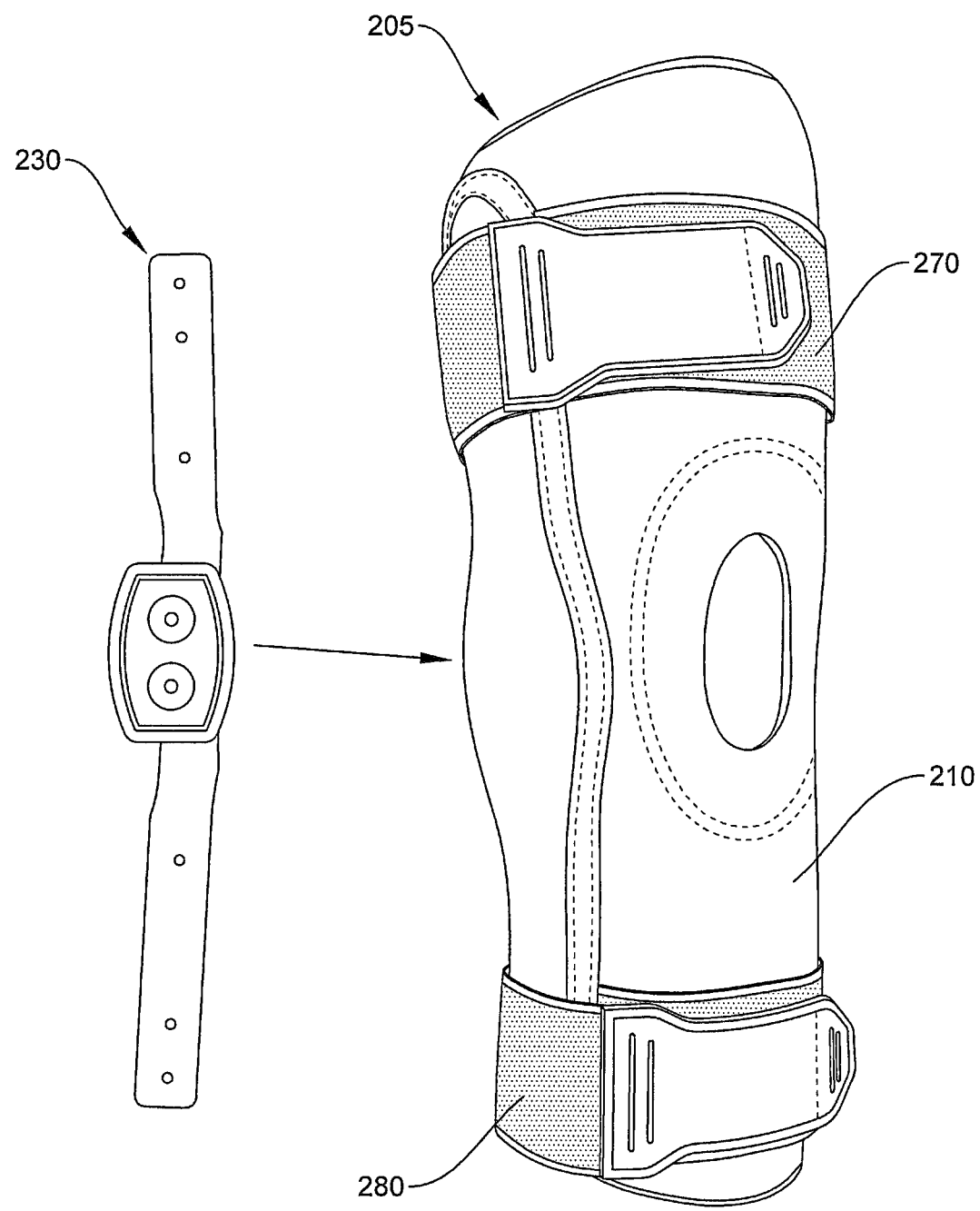
FIG. 28 is an exploded view showing the sleeve of the brace with its straps secured thereabout, but with the hinge member prior to being received into a pocket of the sleeve.

However, the ends 210Ui and 210Uii of the upper portion of the elastic material portion 210 may only be stitched using stitches 210UT that run part-way to the distal end, so that some separation may occur that forms a V-shaped gap at the distal end, as seen in FIG. 27, when the wearer flexes his/her limb with respect to the joint. The unstitched portion of the ends 210Ui and 210Uii that may form the V-shaped opening may have a double layer of poly compression material 210V sewn to each side to provide support that limits the expansion of those unstitched ends to the V-shape shown, while nonetheless allowing the sleeve to adjust constantly to the expansion of the arm during normal movements. Also, the elastic material portion 210 may have a padded annular ring 210R that is configured to surround and provide support to the joint, particularly a knee joint.

Figure 29:
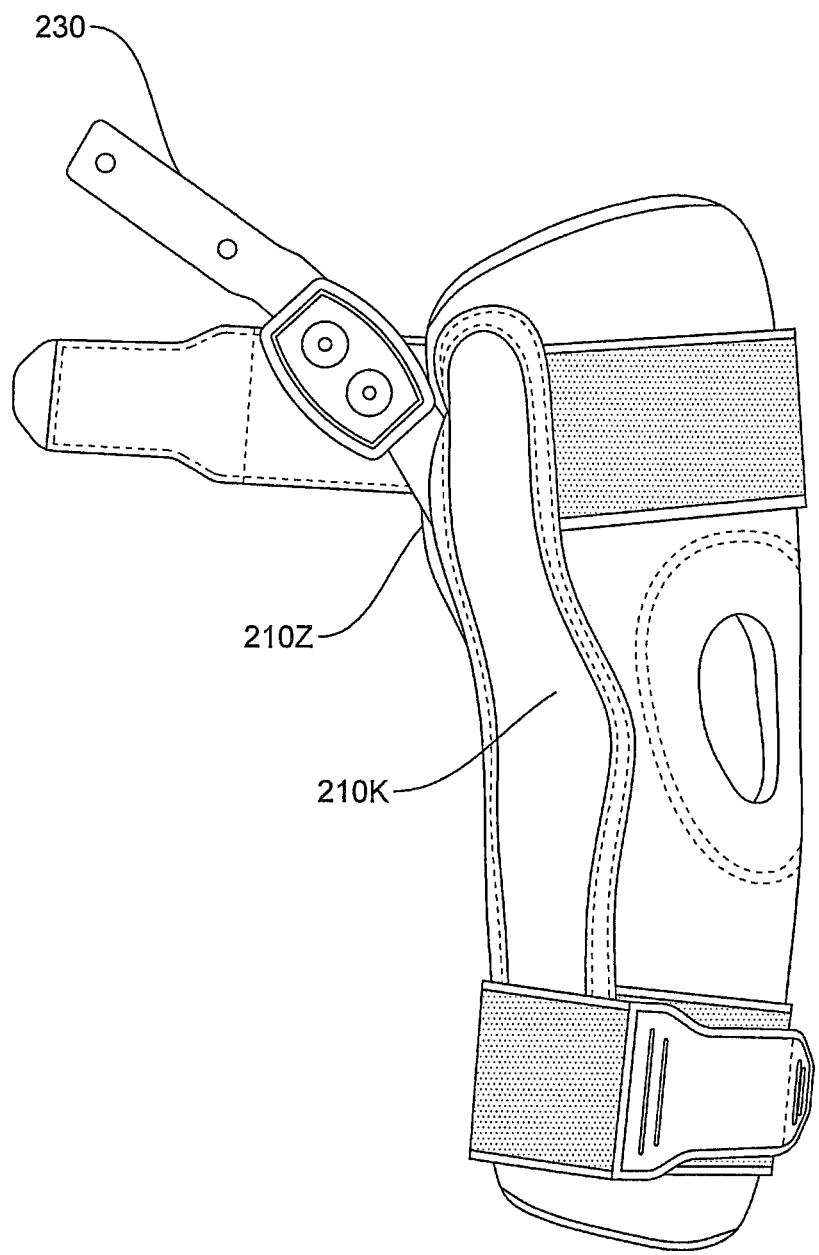
FIG. 29 shows the sleeve of the brace of FIG. 28 as the hinge member is being slid into the pocket through an opening.
Figure 30:
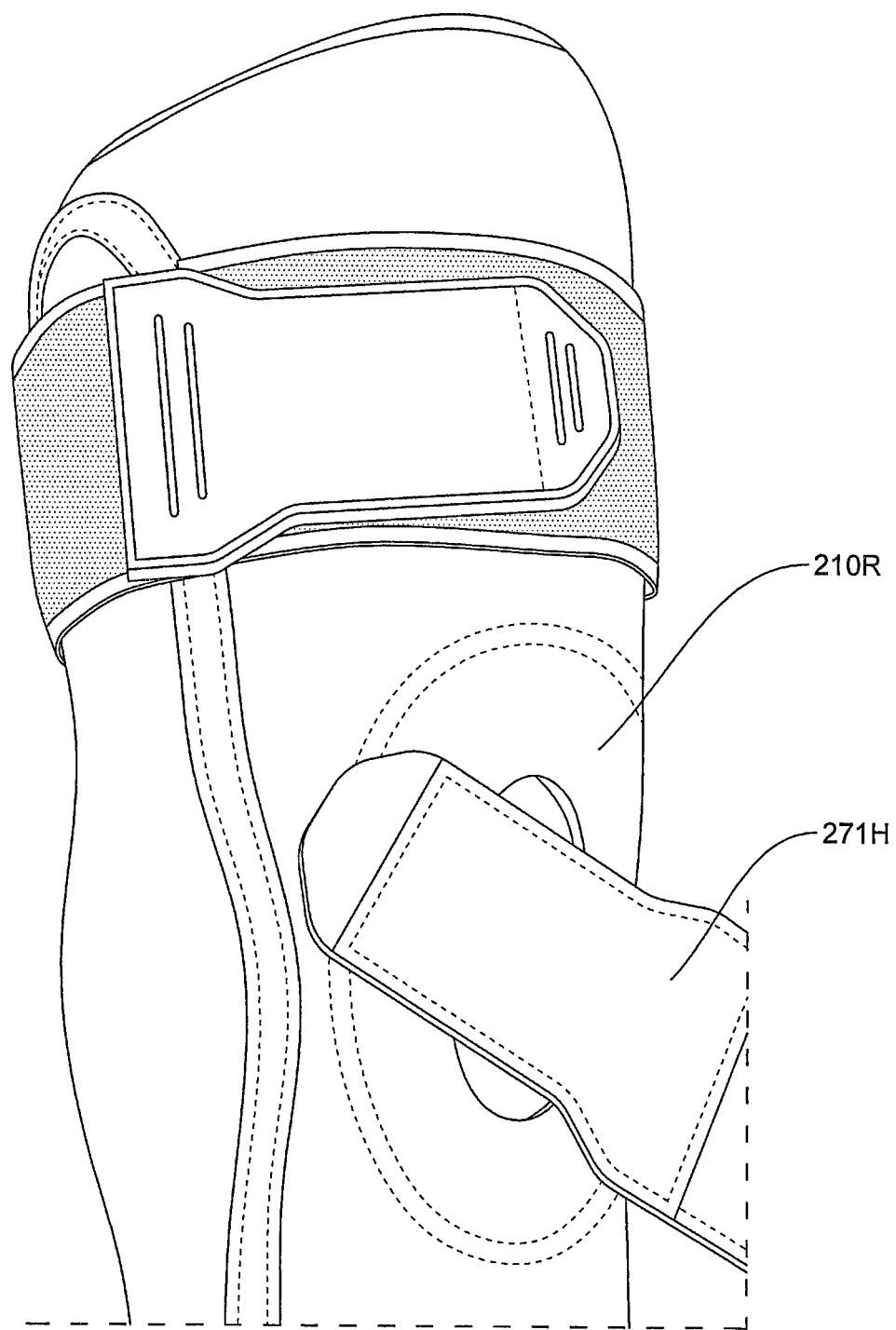
FIG. 30 is an enlarged detail view of the rear side of the end of one of the cinching straps.

The cinching straps 270 and 280 may each have one end be fixedly secured to the elastic material portion 210 using any method of such attachment known in the art, including, but not limited to, stitching, mechanical fasteners (e.g., rivets), etc. The distal (free) end of each of the cinching straps 270 and 280 may be configured to secure to either the sleeve or to the opposite side of the strap itself, after being wrapped around the limb, using hook and loop materials (see FIG. 25). The cinching straps 270 and 280 may also have respective flexible non-elastic members 271 and 281 fixedly secured thereto, the same as the respective flexible non-elastic members 111 and 112 that are used for brace 100. The cinching straps 270 and 280 may each be respectively secured using a small piece of hook (or loop) material (e.g., hook material 271H) that is preferably positioned a small distance away from the distal ends of the respective flexible non-elastic members (see FIG. 30), The hinge member 230 may be secured with respect to the elastic material portion 210 of the sleeve assembly 205 in a unique manner (see FIG. 29) that permits easy replacement of the hinge member, the desirability of which is described hereinabove. The elastic material portion 210 may be formed to include a pocket 210K, which may be shaped to correspond to the periphery of the hinge member 230 (see FIG. 28 and FIG. 29). A small opening may be provided, as shown in FIG. 29, which permits the hinge member 230 to be slid therethrough, and be received into the pocket. The opening may be unsecured, or alternatively, the opening may be releasably secured using a releasable fastening system, including, but not limited to, buttons in button holes, a zipper, etc. A zipper 210Z may be used to provide a large access opening that may be quickly re-secured.

Figure 31:
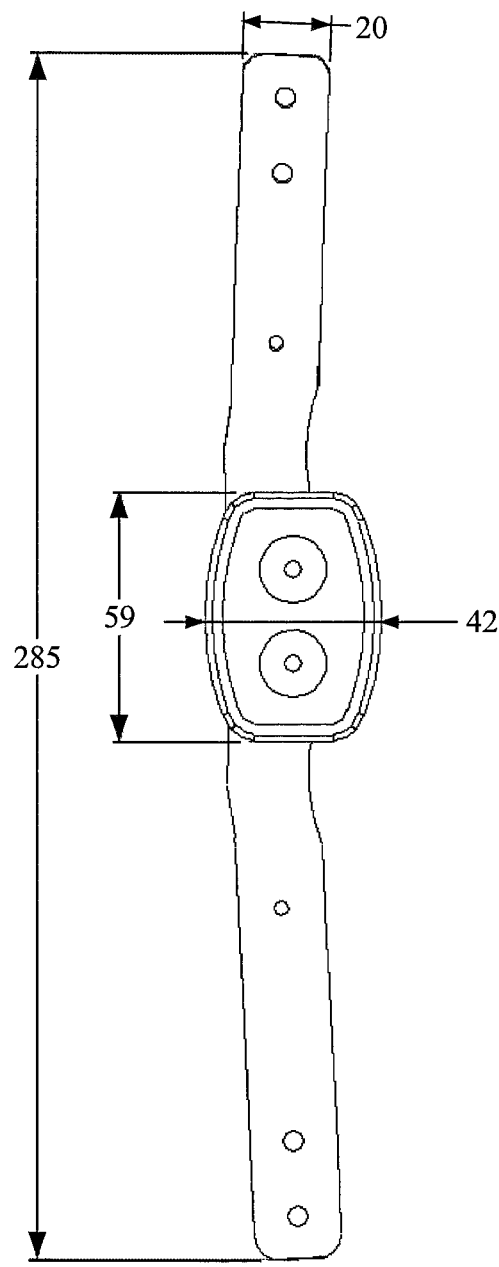
FIG. 31 is a front view of the hinge member of FIG. 28.
Figure 32:
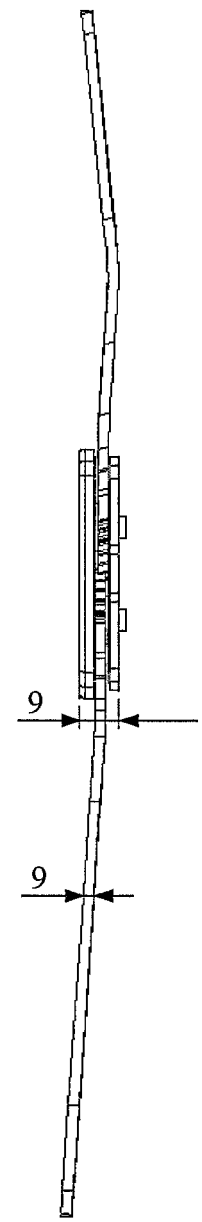
FIG. 32 is a side view of the hinge member of FIG. 31.
Figure 33:
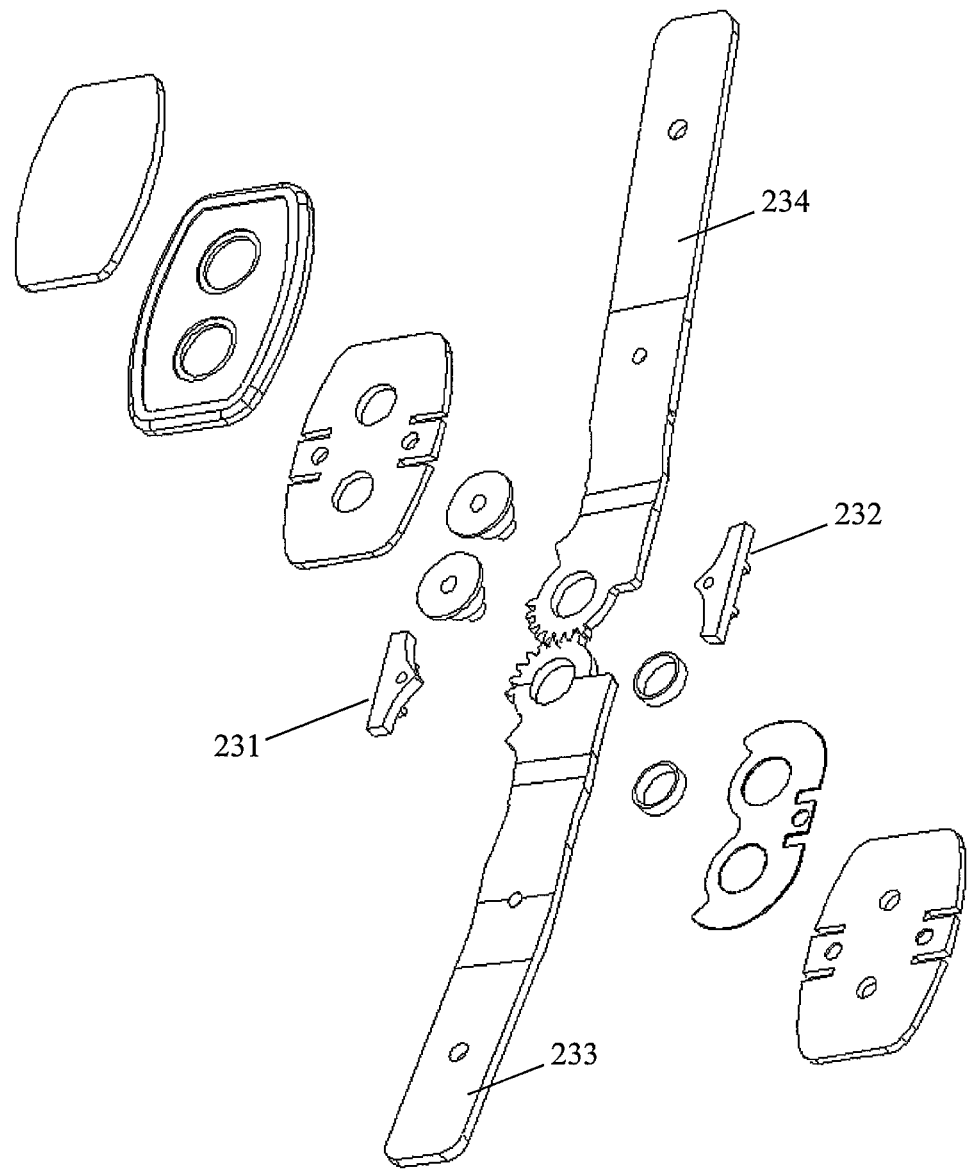
FIG. 33 is an exploded view of the component parts of the hinge member of FIG. 31.

The hinge member 230 shown in FIGS. 31-32 may be formed of the component parts shown in FIG. 33, which may create a bicentric hinge. The hinge member 230 may include fixed stop members 231 and 232 to limit travel of the geared arms 232 and 233 in the flexion and extension movements of the limb.

While illustrative implementations of one or more embodiments of the disclosed apparatus are provided hereinabove, those skilled in the art and having the benefit of the present disclosure will appreciate that further embodiments may be implemented with various changes within the scope of the disclosed apparatus. Other modifications, substitutions, omissions and changes may be made in the design, size, materials used or proportions, operating conditions, assembly sequence, or arrangement or positioning of elements and members of the exemplary embodiments without departing from the spirit of this invention.

Accordingly, the breadth and scope of the present disclosure should not be limited by any of the above-described example embodiments, but should be defined only in accordance with the following claims and their equivalents.

What is claimed is:

1. A knee brace comprising:
an elastic material; a first portion of said elastic material having first and second ends spaced apart a first distance and being fixedly secured together to form a sleeve configured to encircle a leg of a wearer below a knee joint, to apply a first level of compression thereto; a second portion of said elastic material having first and second ends spaced apart a second distance and being configured to form a first flap and a second flap, said second portion of said elastic material configured to circumferentially wrap around the leg of the wearer above the knee joint, said second distance being sufficient for said first flap to overlap onto said second flap; hook and loop materials on said first and second flaps, to releasably secure said first flap to said second flap, to apply a second level of compression thereto;
a secondary flap, said secondary flap having a first end fixedly secured to said second portion of said elastic material, said secondary flap configured to releasably secure to said second flap using hook or loop material, to apply a third level of compression thereto;
wherein said secondary flap is configured for said releasable securement to said second flap in proximity to the knee joint, and said first flap is configured for said releasable securement to said second flap being distally from the knee joint, being above said releasable securement of said secondary flap, and being separated therefrom;
wherein said first flap is configured to angle upwardly for said releasable securement to said second flap;
wherein said secondary flap is configured to angle downwardly for said releasable securement to said second flap; and
wherein said upwardly angled releasable securement of said first flap and said downwardly angled releasable securement of said secondary flap thereby position said first flap and said secondary flap to diverge away from each other, to maintain said knee brace at a proper position on the leg of the wearer.

2. The knee brace according to claim 1, wherein said first flap is angled upwardly with respect to a traverse plane in the range of five degrees and eight degrees; and wherein said secondary flap is angled downwardly with respect to a traverse plane in the range of five degrees and eight degrees.

3. The knee brace according to claim 1, wherein said first flap is angled upwardly with respect to a traverse plane in the range of eight degrees and twelve degrees; and wherein said secondary flap is angled downwardly with respect to a traverse plane in the range of eight degrees and twelve degrees.

4. The knee brace according to claim 1, wherein said first flap is angled upwardly with respect to a traverse plane in the range of twelve degrees and fifteen degrees; and wherein said secondary flap is angled downwardly with respect to a traverse plane in the range of twelve degrees and fifteen degrees.

5. The knee brace according to claim 1, further comprising:

a first flexible non-elastic member, said first flexible non-elastic member fixedly secured to a distal end of said first flap;

a second flexible non-elastic member, said flexible non-elastic member fixedly secured to a distal end of said secondary flap; and wherein said first and second flexible non-elastic members are configured to releasably secure said first flap and said secondary flap to said second flap using said hook and loop materials.

6. The knee brace according to claim 1, further comprising:

an outwardly protruding bulbous shape on a distal end of each of first and second flexible non-elastic members, each configured for grasping by the wearer to unsecure said hook and loop materials.

\* \* \* \* \*